United States Patent
Nebosis et al.

(10) Patent No.: US 8,928,890 B2
(45) Date of Patent: Jan. 6, 2015

(54) SYSTEM FOR OPTICAL COHERENCE TOMOGRAPHY WITH DIFFERENT OPTICAL PROPERTIES OF SPECIMEN AND REFERENCE OBJECTIVES

(75) Inventors: Rainer Nebosis, Munich (DE); Rainer Scheunemann, Munich (DE); Edgar-Gerald Kopp, Merching (DE)

(73) Assignee: Agfa HealthCare N.V., Mortsel (BE)

( * ) Notice: Subject to any disclaimer, the term of this patent is extended or adjusted under 35 U.S.C. 154(b) by 1044 days.

(21) Appl. No.: 12/527,305

(22) PCT Filed: Feb. 20, 2008

(86) PCT No.: PCT/EP2008/052076
§ 371 (c)(1),
(2), (4) Date: Aug. 14, 2009

(87) PCT Pub. No.: WO2008/101963
PCT Pub. Date: Aug. 28, 2008

(65) Prior Publication Data
US 2010/0067022 A1 Mar. 18, 2010

(30) Foreign Application Priority Data
Feb. 21, 2007 (EP) .................................. 07102822

(51) Int. Cl.
*G01B 11/02* (2006.01)
*A61B 5/00* (2006.01)
*G01N 21/47* (2006.01)
*G01B 9/02* (2006.01)
*G01N 21/27* (2006.01)
*G01N 21/45* (2006.01)

(52) U.S. Cl.
CPC .............. *A61B 5/0073* (2013.01); *A61B 5/0066* (2013.01); *G01N 21/4795* (2013.01); *G01B 9/02012* (2013.01); *G01B 9/02002* (2013.01); *G01B 9/02091* (2013.01); *G01B 9/02063* (2013.01); *G01B 9/02072* (2013.01); *G01N 21/274* (2013.01); *G01N 21/45* (2013.01)
USPC ........................................................ 356/497

(58) Field of Classification Search
USPC .................................................. 356/479, 497
See application file for complete search history.

(56) References Cited

U.S. PATENT DOCUMENTS

| | | |
|---|---|---|
| 5,321,501 A | 6/1994 | Swanson et al. |
| 5,465,147 A | 11/1995 | Swanson |

(Continued)

FOREIGN PATENT DOCUMENTS

| | | |
|---|---|---|
| EP | 0 679 611 A1 | 11/1995 |
| EP | 0697611 A2 | 2/1996 |

(Continued)

OTHER PUBLICATIONS

International Preliminary Report on Patentability dated Sep. 8, 2009 from corresponding International Application No. PCT/EP2008/052076, filed on Feb. 20, 2008.

(Continued)

*Primary Examiner* — Hwa Lee
(74) *Attorney, Agent, or Firm* — Keating & Bennett, LLP

(57) ABSTRACT

The invention relates to a system for optical coherence tomography having an interferometer (20) which has a beam splitter (24), a reflector (25), an illumination arm (21), a specimen arm (22) and a reference arm (23).
In order to increase the compactness of the system with at the same time a high image quality a specimen objective is provided in the specimen arm (22) of the interferometer (20) by means of which light is focussed into a focus lying in or on the specimen (1). Moreover, in the reference arm (23) of the interferometer (20) a reference objective is provided by means of which light is focussed onto the reflector (25). The optical properties of the specimen objective differ from the optical properties of the reference objective.

12 Claims, 11 Drawing Sheets

(56) References Cited

U.S. PATENT DOCUMENTS

Figure 1:
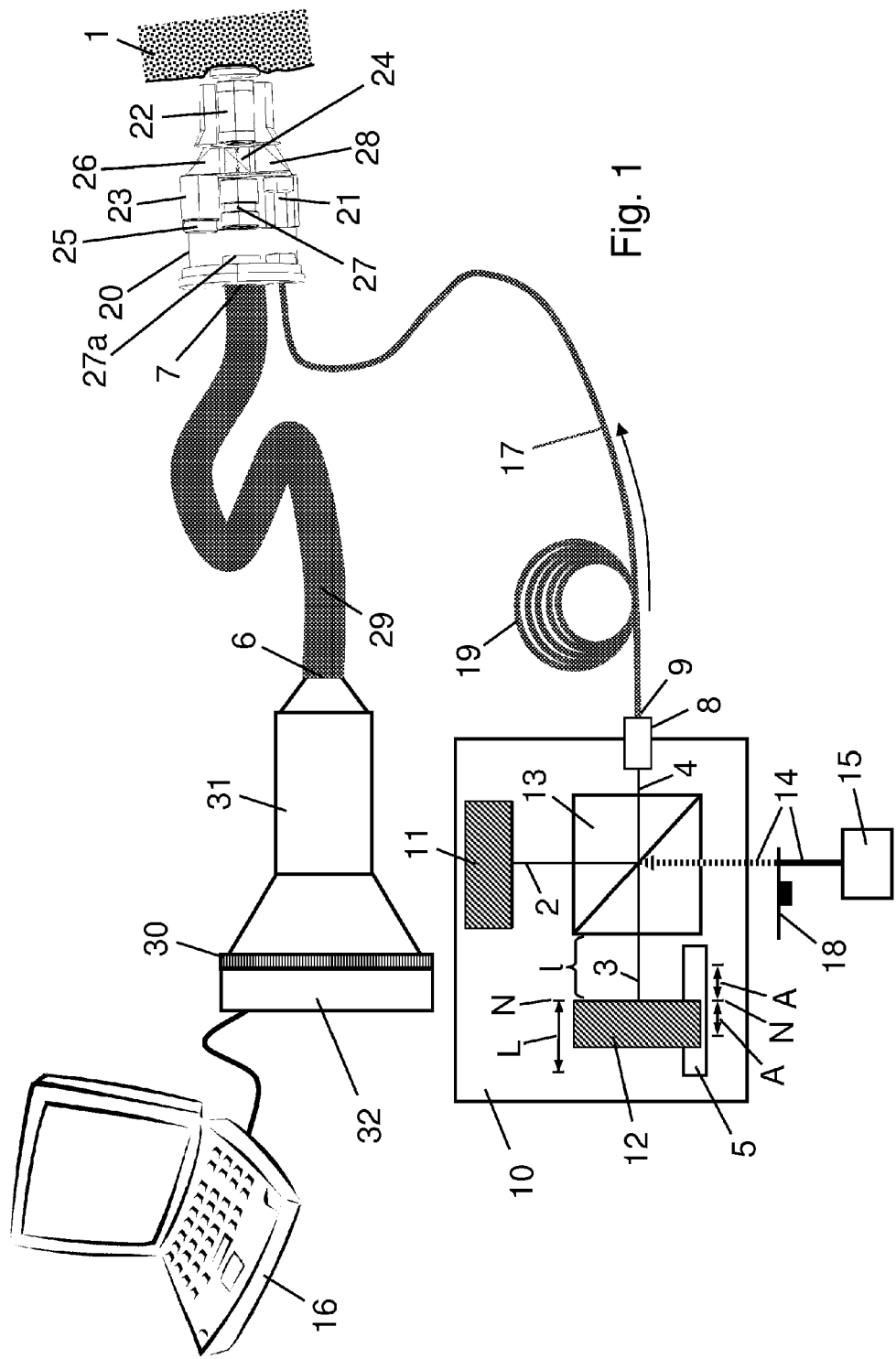

| | | | |
|---|---|---|---|
| 5,555,087 | A | 9/1996 | Miyagawa et al. |
| 5,847,827 | A | 12/1998 | Fercher |
| 5,975,697 | A | 11/1999 | Podoleanu et al. |
| 6,485,413 | B1 | 11/2002 | Boppart et al. |
| 6,552,806 | B1 | 4/2003 | Swinford et al. |
| 6,608,717 | B1 | 8/2003 | Medford et al. |
| 6,810,175 | B1 | 10/2004 | Wey et al. |
| 6,895,149 | B1 | 5/2005 | Jacob et al. |
| 7,088,454 | B2 | 8/2006 | Chang et al. |
| 7,236,251 | B2* | 6/2007 | Takaoka .................. 356/497 |
| 7,345,770 | B2 | 3/2008 | Chan et al. |
| 7,408,649 | B2* | 8/2008 | Freischlad et al. .......... 356/497 |
| 7,450,243 | B2 | 11/2008 | Marks et al. |
| 7,474,407 | B2 | 1/2009 | Gutin |
| 8,199,327 | B2 | 6/2012 | Nebosis et al. |
| 8,330,962 | B2 | 12/2012 | Nebosis et al. |
| 8,339,610 | B2 | 12/2012 | Nebosis et al. |
| 8,526,006 | B2 | 9/2013 | Nebosis et al. |
| 8,559,016 | B2 | 10/2013 | Nebosis |
| 8,593,639 | B2 | 11/2013 | Nebosis |
| 2002/0037149 | A1 | 3/2002 | Chen |
| 2002/0048025 | A1 | 4/2002 | Takaoka |
| 2002/0070350 | A1 | 6/2002 | Rushbrooke et al. |
| 2003/0048454 | A1 | 3/2003 | Prinzhausen et al. |
| 2003/0076506 | A1 | 4/2003 | Fercher |
| 2003/0135205 | A1 | 7/2003 | Davenport et al. |
| 2003/0199769 | A1 | 10/2003 | Podoleanu et al. |
| 2004/0239946 | A1 | 12/2004 | Kane et al. |
| 2005/0018201 | A1 | 1/2005 | de Boer et al. |
| 2005/0185192 | A1 | 8/2005 | Kim et al. |
| 2005/0219544 | A1 | 10/2005 | Chan et al. |
| 2005/0219545 | A1 | 10/2005 | Chan et al. |
| 2006/0158655 | A1 | 7/2006 | Everett et al. |
| 2006/0170930 | A1 | 8/2006 | Li |
| 2006/0215170 | A1* | 9/2006 | Toida et al. ............. 356/479 |
| 2006/0285122 | A1 | 12/2006 | Bankhead et al. |
| 2007/0165234 | A1 | 7/2007 | Podoleanu |
| 2007/0273713 | A1 | 11/2007 | Wubben et al. |
| 2008/0024767 | A1* | 1/2008 | Seitz ......................... 356/73 |
| 2010/0027020 | A1 | 2/2010 | Nebosis |
| 2010/0027029 | A1 | 2/2010 | Nebosis et al. |
| 2010/0033726 | A1 | 2/2010 | Nebosis et al. |
| 2010/0091295 | A1 | 4/2010 | Nebosis et al. |
| 2010/0149543 | A1 | 6/2010 | Nebosis et al. |
| 2010/0166293 | A1 | 7/2010 | Sugita et al. |
| 2010/0280315 | A1 | 11/2010 | Pan |

FOREIGN PATENT DOCUMENTS

| | | |
|---|---|---|
| EP | 0 956 809 A1 | 11/1999 |
| EP | 1962049 A1 | 8/2008 |
| EP | 1962050 A1 | 8/2008 |
| EP | 1962051 A1 | 8/2008 |
| EP | 1962052 A1 | 8/2008 |
| EP | 1962079 A1 | 8/2008 |
| EP | 1962080 A1 | 8/2008 |
| EP | 1962081 A1 | 8/2008 |
| EP | 1962082 A1 | 8/2008 |
| EP | 2199734 A1 | 8/2008 |
| EP | 2267403 A3 | 4/2011 |
| EP | 2339329 A2 | 6/2011 |
| EP | 2365316 A1 | 9/2011 |
| WO | 03/089962 A2 | 10/1993 |
| WO | 95/33970 A1 | 12/1995 |
| WO | 2006/102997 A1 | 10/2006 |
| WO | 2006/118619 A1 | 11/2006 |

OTHER PUBLICATIONS

Anyuan, "Study on Theory and Experiment of Optical Coherence Tomography and Broad-Band Light Source," Ph.D. Thesis, Tianjin University, 2003, pp. 57, 76-77.

European Search Report, completed on Jun. 8, 2011, from corresponding European Application No. EP 11 00 2234.

Anonymous, "Leached Bundles" Internet Article, Aug. 15, 2004, URL: http://www.us.schott.com/fiberoptics/english/products/healthcare/imagingfiberoptics/flexiblecomponents/leached.html.

Beer, S., et al., "Video-rate Optical Coherence Tomography Imaging with Smart Pixels," Proceedings of the SPIE—the International Society for Optical Engineering SPIE—Int. Soc. Opt. Eng. USA, vol. 5140, No. 1, 2003, pp. 69-76.

Chiarulli, D. M., et al, "Optoelectronic Multichip Modules Based on Imaging Fiber Bundle Structures," Proceedings of the SPIE—the International Society for Optical Engineering SPIE—INT. Soc. Opt. Eng. USA, vol. 4089, 2000, pp. 80-85.

Cobb, M. J., et al., "Continuous Focus Tracking for Real-Time Optical Coherence Tomography," Optics Letters, OSA, Optical Society of America, Washington, DC, US, vol. 30, No. 13, Jul. 1, 2005, pp. 1680-1682.

Dubois, A., et al., Ultrahigh-Resolution Full-Field Optical Coherence Tomography, Applied Optics Opt. Soc. America USA, vol. 43, No. 14, May 10, 2004, pp. 2874-2883.

Egan, P., et al., "Full-Field Optical Coherence Tomography with a Complimentary Metal-Oxide Semiconductor Digital Signal Processor Camera," Optical Engineering, vol. 45, Jan. 2006, pp. 01560-1-015601-6.

Ford, H. D., et al., "Full-Field Optical Coherence Tomography using a Fibre imaging Bundle," Proc. of SPIE, vol. 6079, 2006, pp. 60791H-1-60791H-9.

Grieve, K., et al., "In Vivo Anterior Segment Imaging in the Rat Eye with High Speed White Light Full-Field Optical Coherence Tomography," Optics Express Opt. Soc. America, USA, vol. 13, No. 16, Aug. 8, 2005, pp. 6286-6295.

Kim, J, et al., "Optical Coherence Tomography Speckle Reduction by a Partially Spatially Coherent Source," Journal of Biomedical Optics, SPIE, USA, vol. 10, No. 6, Nov. 2005, pp. 64034-1-64034-9.

Lexer, F., et al., "Dynamic Coherent Focus OCT with Depth-Independent Transversal Resolution," Journal of Modern Optics, vol. 46, No. 3, 1999, pp. 541-553.

Oh, W. Y., et al., Spectrally-Modulated Full-Field Optical Coherence Microscopy for Ultrahigh-Resolution Endoscopic Imaging, Optics Express Opt. Soc. America USA, vol. 14, No. 19, Sep. 2006, pp. 8675-8684.

Szydlo, J., et al., Rapid Communication: High-speed Measurements in Optical Low-Coherence Reflectometry, Measurement Science and Technology, Institute of Physics Publishing, Bristol, GB, vol. 9, No. 8, Aug. 1, 1998, pp. 1159-1162.

Tearney, G. J., et al., "In Vivo Endoscopic Optical Biopsy with Optical Coherence Tomography," Science, American Association for the Advancement of Science, US, vol. 276, No. 5321, Jun. 27, 1997, pp. 2037-2039.

Teramura, Y., et al., "Two-Dimensional Optical Coherence Tomography Using Spectral Domain Interferometry," Journal of Optics. A: Pure and Applied Optics, Institute of Physics Publishing, Bristol, GB, vol. 2, No. 1, Jan. 1, 2000, pp. 21-26.

Watanabe, Y., et al., "Three-Dimensional Imaging by Ultrahigh-Speed Axial-Lateral Parallel Time Domain Optical Coherence Tomography," Optics Express Opt. Soc. America USA, vol. 14, No. 12, Jun. 2006, pp. 5201-5209.

Wojtkowski, M., et al., "Real-time in Vivo Imaging by High-Speed Spectral Optical Coherence Tomography," Optics Letters, OSA, Optical Society of America, Washington, D.C., US, vol. 28, No. 19, Oct. 1, 2003, pp. 1745-1747.

International Search Report dated Apr. 10, 2008, from counterpart International Application No. PCT/EP2008/052076, filed Feb. 20, 2008.

Dubois, A. et al., "High-Resolution Full-Field Optical Coherence Tomography with a Linnik Microscope," Applied Optics, vol. 41, No. 4, Feb. 1, 2002, pp. 805-812.

Grieve, K., et al., "Ocular Tissue Imaging Using Ultrahigh-Resolution, Full-Field Optical Coherence Tomography," Investigative Ophthalmology & Visual Science, vol. 45, No. 11, Nov. 2004, pp. 4126-4131.

Fowles, Grant R., Introduction to Modern Optics, 1975, Holt Rinehart, 2nd ed., pp. 16-17.

(56) References Cited

OTHER PUBLICATIONS

Schmit J., et al., "Extended averaging technique for derivation of error-compensating algorithms in phase-shifting interferometry," Applied Optics, vol. 34, No. 19, Jul. 1, 1995, pp. 3610-3619.

Watanabe, Y. et al., "Full-field optical coherence tomography by achromatic phase sifting with a rotating polarizer," Applied Optics, vol. 44, No. 8, Mar. 10, 2005, pp. 1387-1392.

Watanabe, Y., et al., "In vivo non-mechanical scanning grating-generated optical coherence tomography using an InGaAs digital camera," Optics Communicaters 261, 2006, pp. 376-380.

Watanabe, Y., et al., "Three-dimensional wide-field optical coherence tomography using an ultrahigh-speed CMOS camera," Optics Communications 281, 2008, pp. 1889-1895.

European Search Report, completed on Jun. 8, 2011, from European Application Publication No. EP 2 365 316.

* cited by examiner

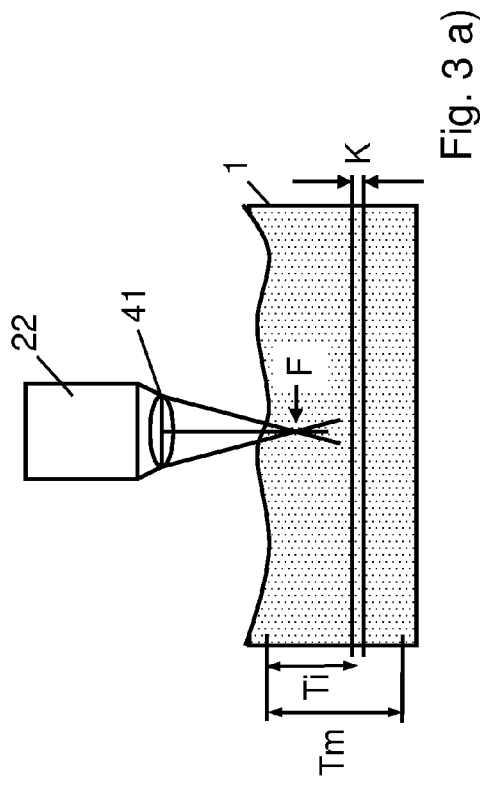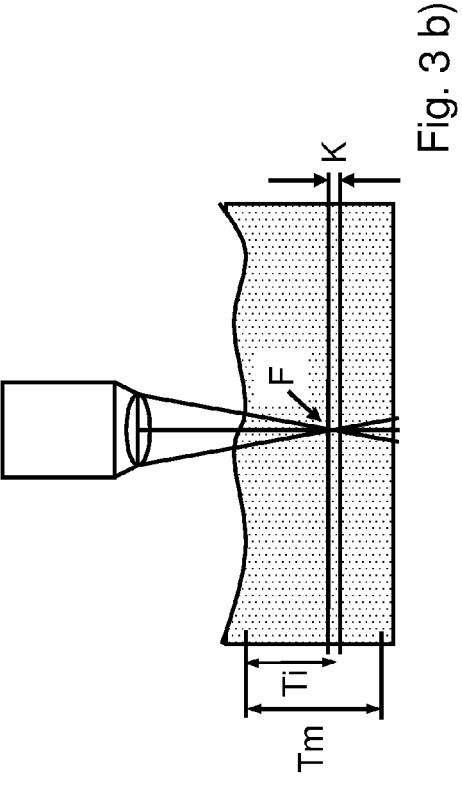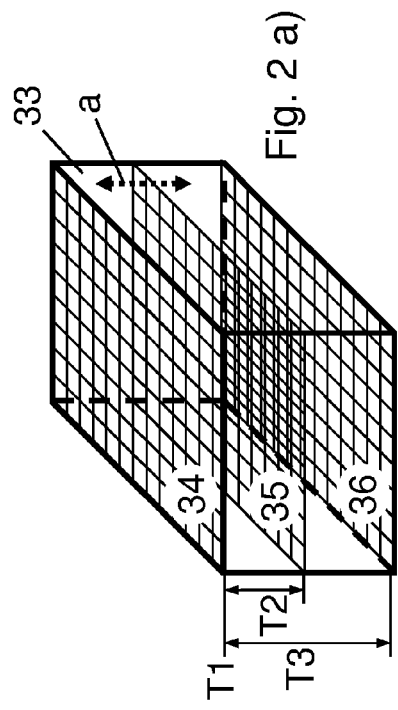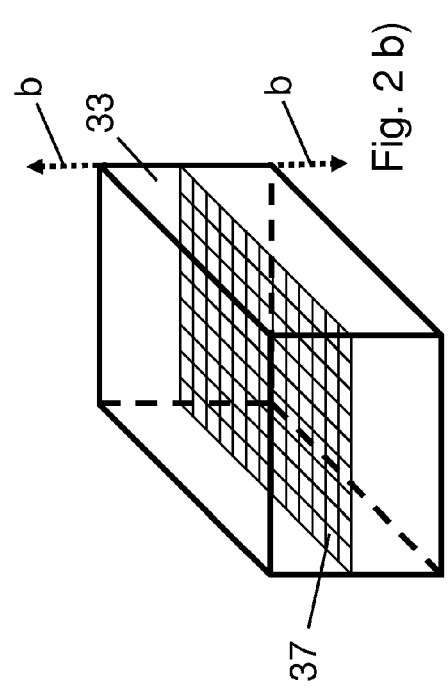

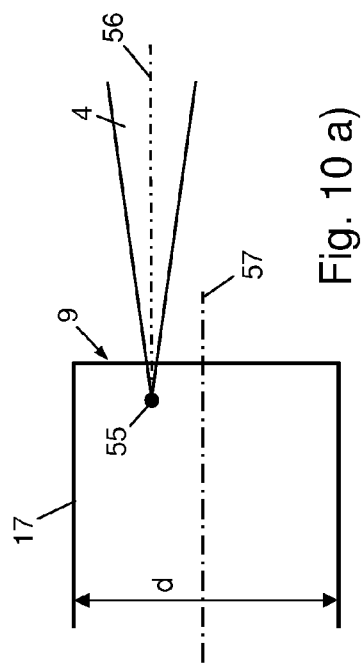
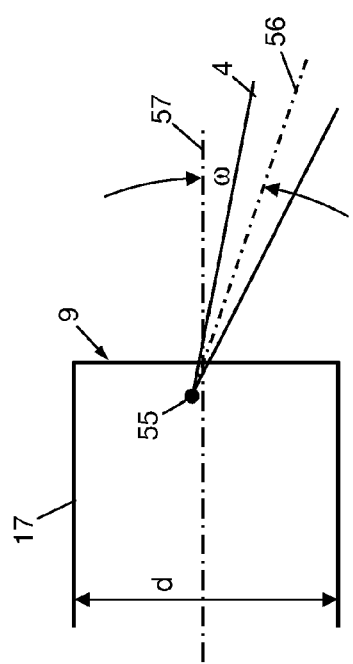
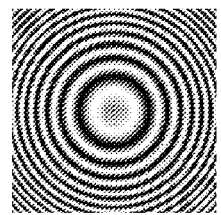
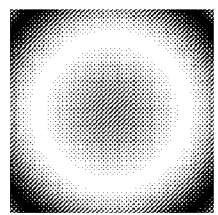
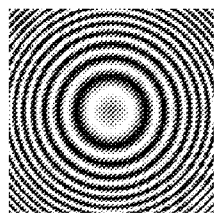
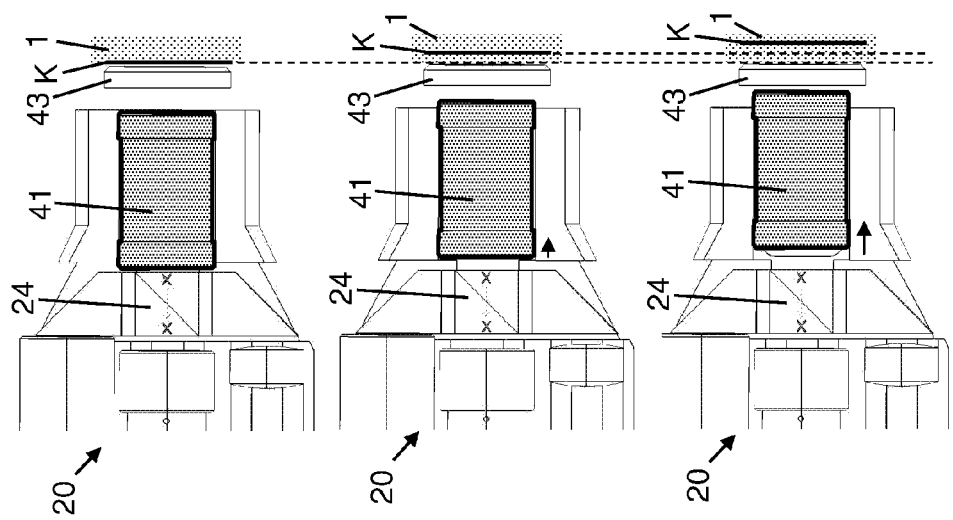

SYSTEM FOR OPTICAL COHERENCE TOMOGRAPHY WITH DIFFERENT OPTICAL PROPERTIES OF SPECIMEN AND REFERENCE OBJECTIVES

The application relates to a system for optical coherence tomography.

Optical coherence tomography (OCT) is a method of measuring light-scattering specimens on their inside. Due to its light-scattering properties biological tissue is particularly suitable for diagnostic examination by means of OCT. Since for OCT relatively low light intensities are sufficient and the wavelengths of the light used mostly come within the near infrared range (750 nm to 1350 nm), unlike ionising X-ray diagnostics it does not contaminate biological tissue with radiation. It is therefore particularly significant for medicine and is roughly comparable to ultrasound diagnostics. With OCT, instead of sound, broadband light which has a very short coherence length is used. The running times of the light reflected on different boundary layers within the specimen are recorded with the aid of an interferometer. With OCT, typically resolutions higher by one to two orders of magnitude are to be achieved than with ultrasound, but the measuring depth achievable is considerably smaller. Due to optical scattering the cross-section images obtained only reach into the tissue up to a depth of a few millimeters. The currently most important areas of application of OCT are in opthalmology, dermatology and the diagnosis of cancer. However, there are also some non-medical applications, such as e.g. in materials testing.

A generic system is known from W. Y. Oh et al., OPTICS EXPRESS Vol. 14, No. 19 (2006) 8675-8684 wherein the light emitted by a xenon arc lamp is injected into a Michelson interferometer, spectrally modulated by shifting a reflector located on a piezoelectric converter, and conveyed to a Linnik interferometer, from which it impinges on the specimen to be examined. Structurally identical lenses are respectively provided in the specimen and reference arm of the Linnik interferometer.

In order to obtain a measuring head which is particularly suitable for endoscopic applications, the Linnik interferometer described by W. Y. Oh et al. would have to be more compact in design without the image quality being negatively affected by this.

It is the object of the invention to specify a system for optical coherence tomography wherein the measuring head is as compact as possible in design and at the same time guarantees a high image quality.

This object is achieved according to claim 1 in that a specimen objective is provided in the specimen arm by means of which light of the partial beam extending through the specimen arm is focussed in a focus lying on or in the specimen, and a reference objective is provided in the reference arm by means of which light of the partial beam extending through the reference arm is focussed onto a reflector, the optical properties of the specimen objective differing from the optical properties of the reference objective, and by a system for optical coherence tomography comprising an interferometer which has a beam splitter, a reflector, an illumination arm, a specimen arm and a reference arm, light being injected into the interferometer by the illumination arm and split by the beam splitter into a partial beam extending through the reference arm towards the reflector and a partial beam extending through the specimen arm towards the specimen, the partial beams being reflected by the reflector and by the specimen, respectively, and the reflected partial beams being superposed in the beam splitter to form a further partial beam the light of which can be collected by a detector, a specimen objective provided in the specimen arm by means of which light of the partial beam extending through the specimen arm is focussed in a focus lying on or in the specimen, and a reference objective provided in the reference arm by means of which light of the partial beam extending through the reference arm is focussed onto the reflector, the optical properties of the specimen objective differing from the optical properties of the reference objective.

The invention is based upon the idea of producing different optical properties of the specimen and reference objective by a corresponding choice of lenses with a different number and/or with different focal distances and/or different distances in relation to one another. Due to the different design of the specimen and reference objective according to the invention, on the one hand different distances between the specimen and reference objective and the beam splitter can easily be produced. For example, in this way the specimen objective can be disposed considerably closer to the beam splitter, by means of which the diameter of the specimen objective, in particular of the lenses located in the specimen objective, can be significantly reduced in comparison with the systems known from the prior art, without however appreciably reducing the light intensity of the specimen objective and so the light yield when collecting the light reflected by the specimen. On the other hand, by means of the invention the reference objective can be disposed a considerably larger distance away from the beam splitter, by means of which folding of the reference arm is made possible with which the reference arm is tilted by 90° in relation to its position in a non-folded Linnik interferometer.

By means of the "asymmetrical" design according to the invention of the interferometer a very slim and compact form of the measuring head is achieved, and at the same time it is guaranteed that the light reflected by the specimen is collected with high efficiency, and so a high image quality can at the same time be guaranteed.

In one preferred embodiment of the invention provision is made such that the specimen objective has a first focal distance and the reference objective a second focal distance, the first focal distance of the specimen objective differing from the second focal distance of the reference objective. In this way different optical paths can easily be produced in the specimen and reference arm.

Preferably, the optical path through the reference objective is shorter than the optical path through the specimen objective. In this way the optical path in the reference arm outside of the reference objective can be chosen to be longer, by means of which the larger distances between the reference objective and the beam splitter required for folding the reference arm of the interferometer can be produced particularly easily.

It is preferred here that the difference between the optical paths through the reference objective and the specimen objective is at least twice as large as the maximum optical scan depth in the specimen. Here the maximum optical scan depth specifies the depth range within which interference can occur between the partial beam reflected by the specimen in this depth range and the partial beam reflected by the reflector. In this way clear and simple allocation of the image information recorded at a specific depth in the specimen is guaranteed. This applies in particular to OCT systems with a so-called pre-modulator in which the light is spectrally modulated before it is injected into the interferometer.

It is preferred that the position of the specimen objective relative to the beam splitter differs from the position of the reference objective relative to the beam splitter. Preferably, the optical path between the reference objective and the beam splitter is larger here than the optical path between the specimen objective and the beam splitter. By means of this embodiment folding of the reference arm and/or the illumination arm, and so greater compactness of the interferometer is made possible.

Preferably, the specimen objective is moveably mounted in the specimen arm so that the distance between the specimen objective and the beam splitter can be changed. In this way the focus of the specimen objective can always come within a depth range of the specimen in which interference occurs.

Preferably, at least part of the optical axis of the reference arm and/or of the illumination arm encloses an angle, which is different from 90°, with the optical axis of the specimen arm. Preferably, at least part of the optical axis of the reference arm and of the illumination arm extends parallel here to the optical axis of the specimen arm. By means of this folding the interferometer can be particularly compact in design.

It is preferred that a deflection element is provided in the reference arm or illumination arm for deflecting the partial beam extending through the reference arm or illumination arm. Preferably, the deflection element comprises a deflection prism. In this way adjustment-free and precise folding of the reference and illumination arm is made possible.

It is preferred that the interferometer has an outlet arm with at least one optical element and the outlet arm together with the specimen and reference objective forms specimen optics and reference optics, respectively, the specimen optics and/or reference optics being telecentric. Telecentric optics are characterised in that the object distance can be varied without the image size changing.

It is preferred that the specimen objective has a larger numerical aperture than the reference objective. This is particularly advantageous with a folded Linnik interferometer because in this way the reference objective can be matched relatively easily to the specimen objective and, moreover, be particularly compact in design.

Preferably, the interferometer comprises an illumination arm which has at least one optical element and together with the specimen or reference objective forms illumination optics with a numerical aperture, and the interferometer has an outlet arm which has at least one optical element and together with the specimen objective forms specimen optics with a numerical aperture, the numerical aperture of the illumination optics being smaller than the numerical aperture of the specimen optics. In this way one gains the advantage that also the light reflected on inclined specimen structures is collected by the specimen objective because the acceptance angle of the specimen objective is larger than the divergence angle of the illumination ball. If, however, the numerical aperture for illumination and imaging were of equal size, with the reflection on inclined specimen structures less light would be collected than with the reflection on structures which are perpendicular to the optical axis.

In a further advantageous embodiment of the invention provision is made such that the detector comprises a plurality of detector elements, two respective adjacent detector elements having a centre-centre distance, and the specimen objective and the reference objective being designed such that the distance between two consecutive interference minima or interference maxima of an interference pattern occurring is greater for all scan depths than the centre-centre distance between the detector elements. In this way the interference structures are always recorded with a high level of reliability at every depth of the spatial element of the specimen observed. In this way information losses are avoided and so a high image quality is guaranteed.

Within the context of the invention, irradiation of the specimen with the light emitted by the interferometer is to be understood as meaning that the light emitted by the interferometer, which comprises the moveable reflector, impinges on the specimen directly or only impinges on the specimen after having passed through a further interferometer which is disposed between the interferometer and the specimen.

Within the context of the invention, collection of the light reflected by the specimen, in particular at different depths of the specimen, by the detector or the detector elements is to be understood as meaning that the detector or the detector elements collect the light from manifestations of interference which are produced upon superposition of the light reflected by the specimen, in particular at different depths of the specimen, with the light reflected on a reference mirror. The superposition of the light can take place here either in the interferometer which comprises the moveable reflector or in a further interferometer.

Figure 4:
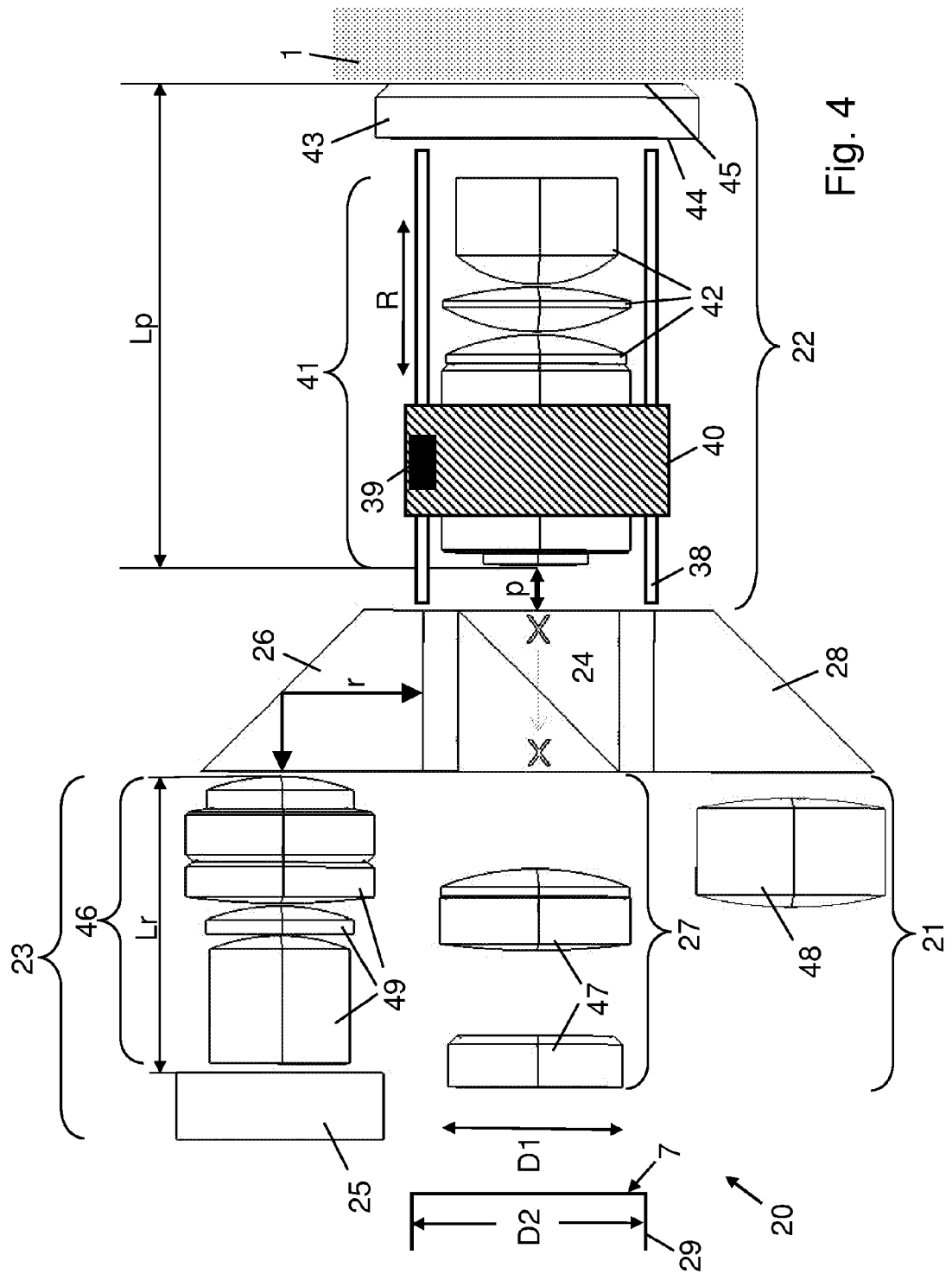
Figure 5:
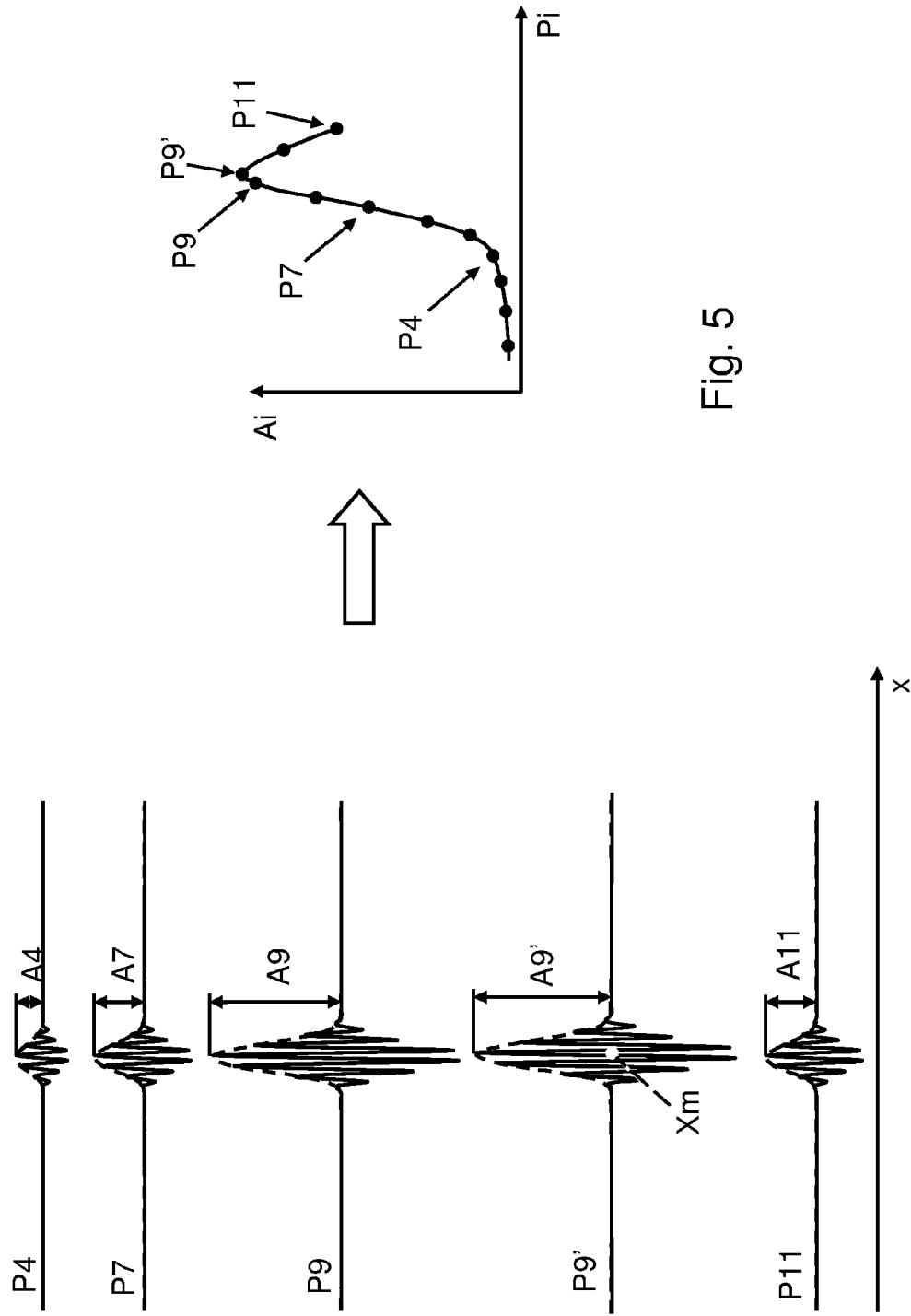
Figure 6:
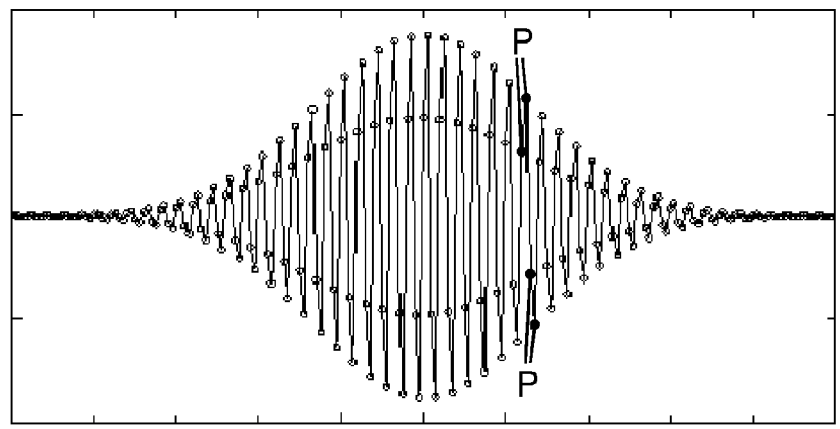
Figure 6:
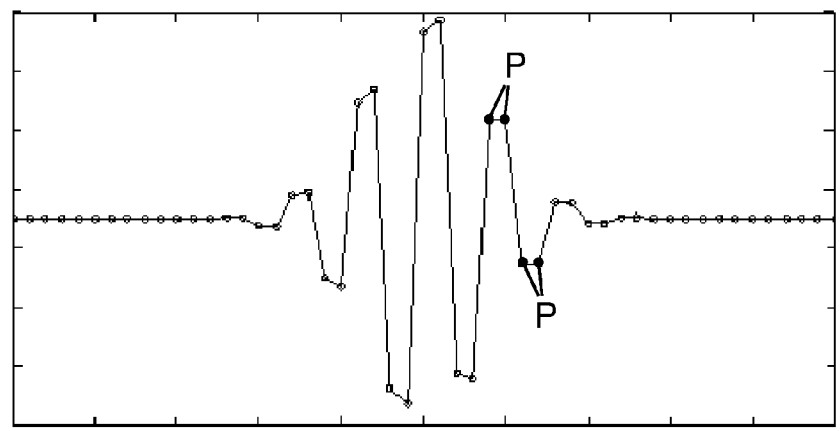
Figure 6:
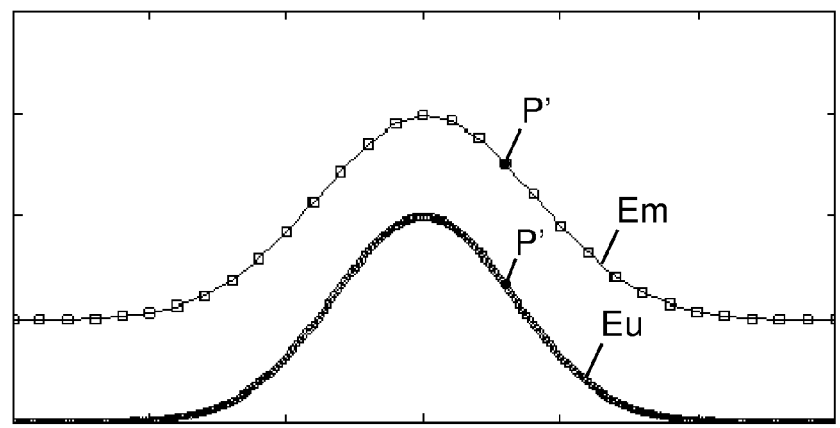
Figure 7:
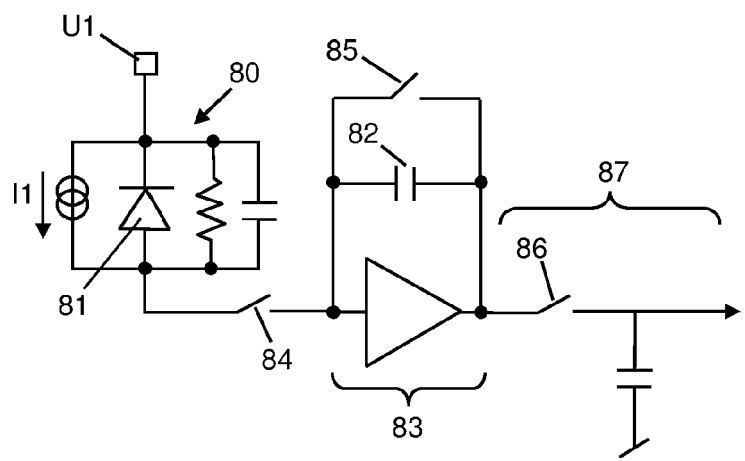
Figure 8:
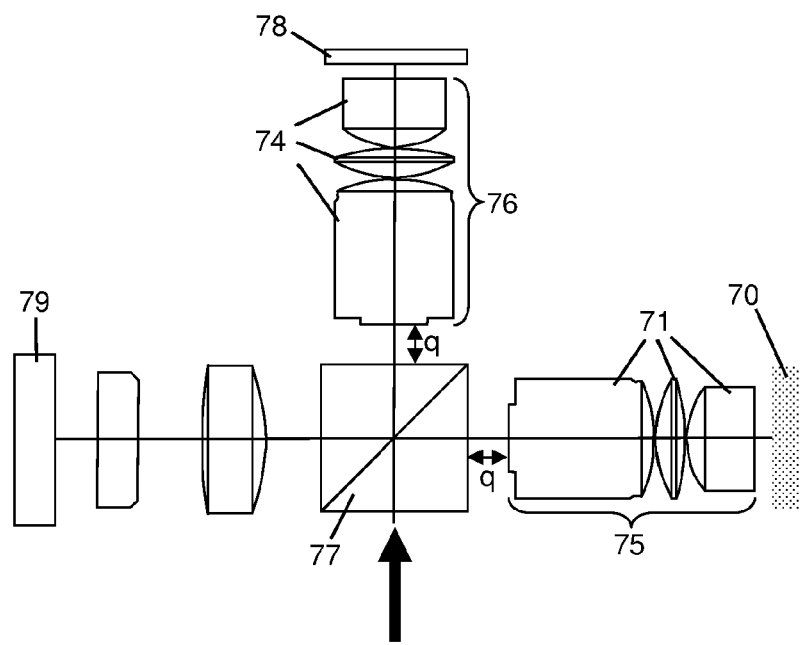
Figure 11:
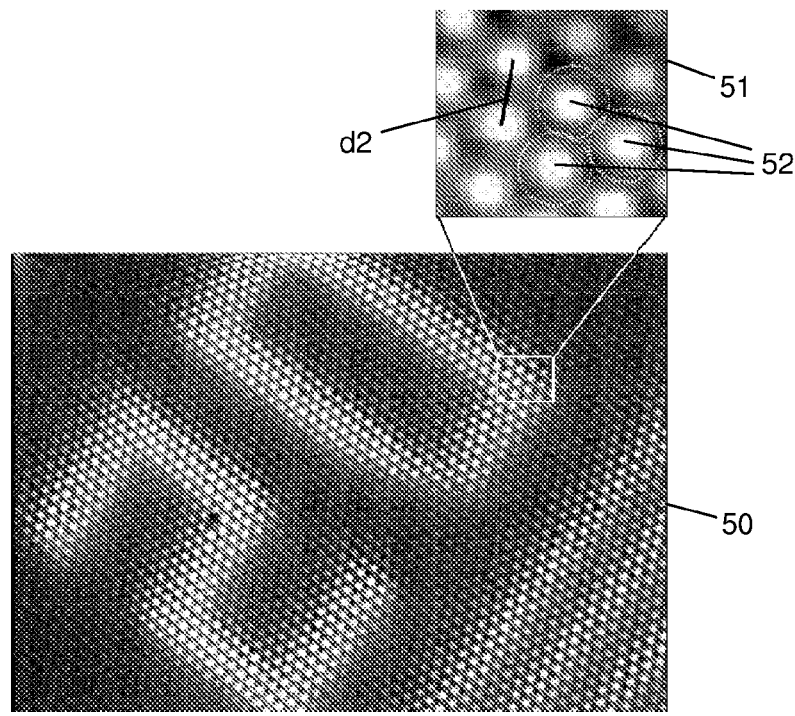
Figure 12:
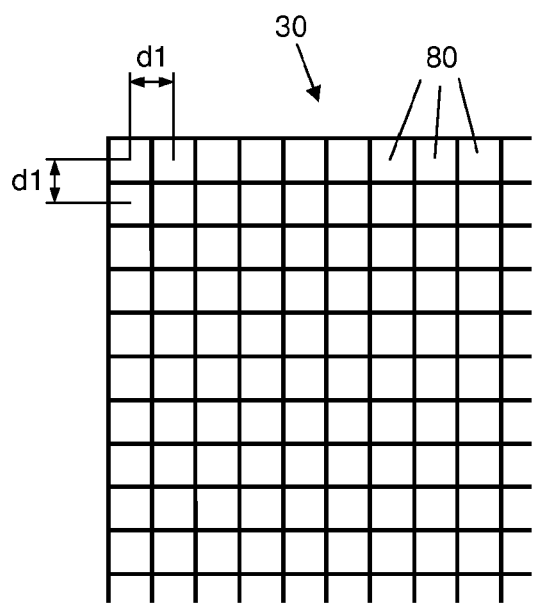
Figure 13:
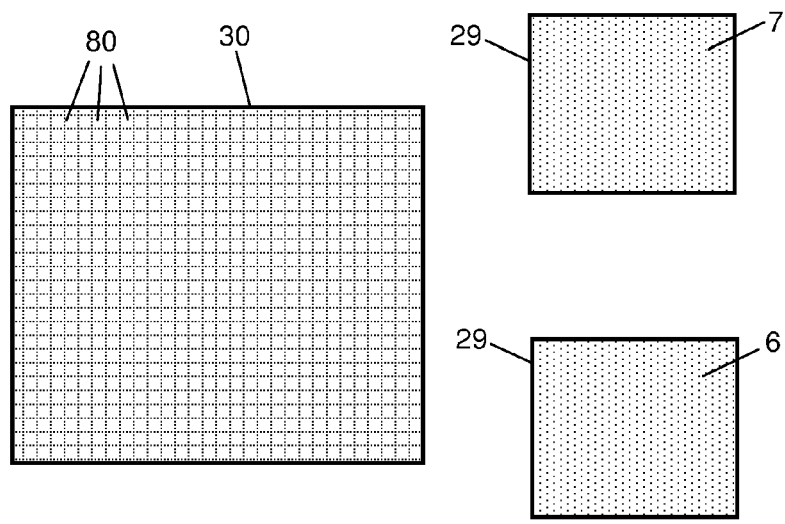
Figure 14:
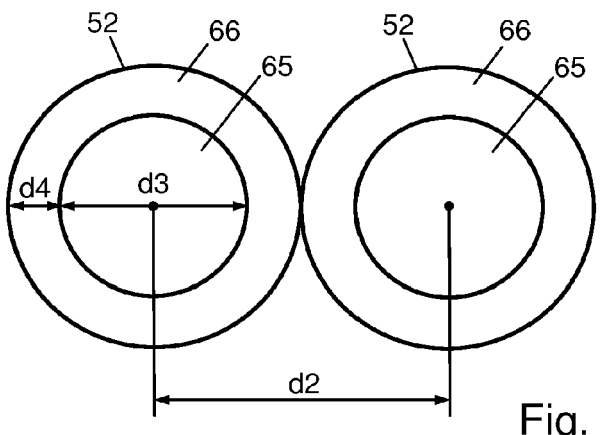
Figure 14:
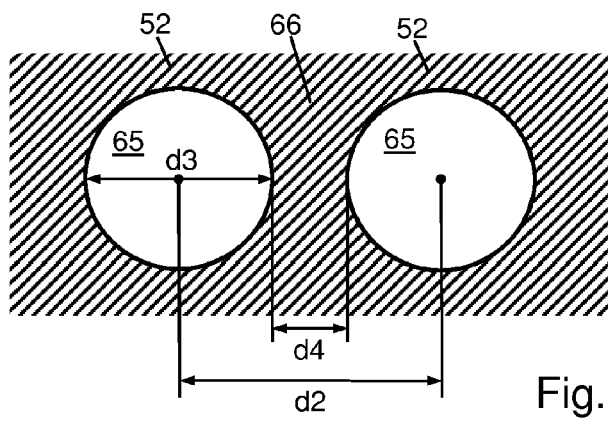
Figure 15:
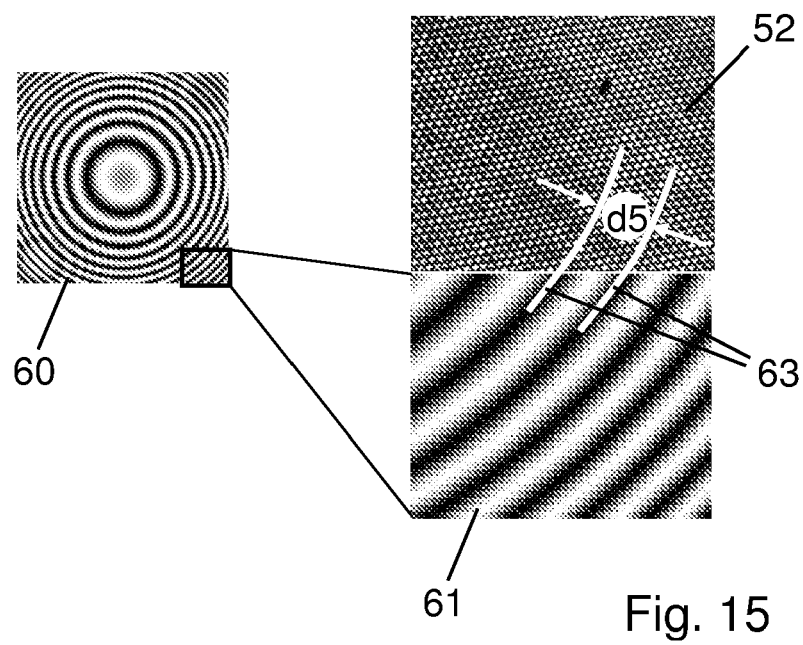
Figure 16:
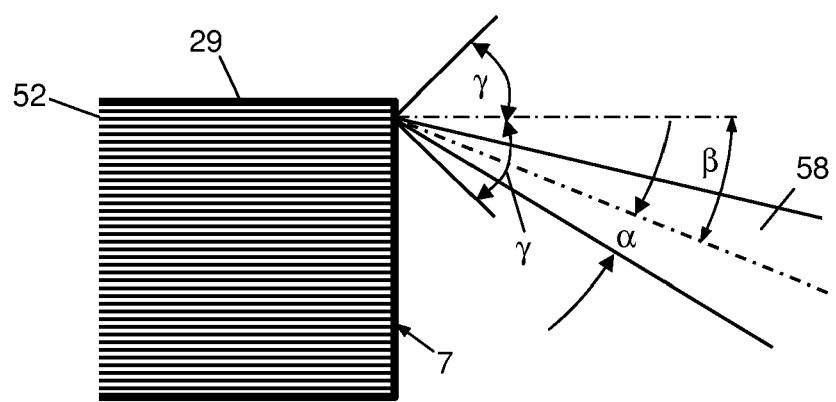
Figure 17:
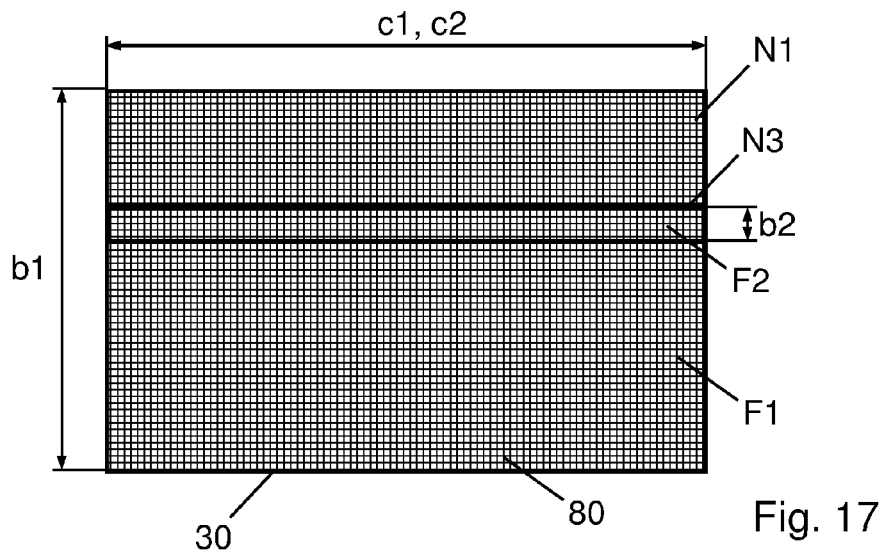
Figure 18:
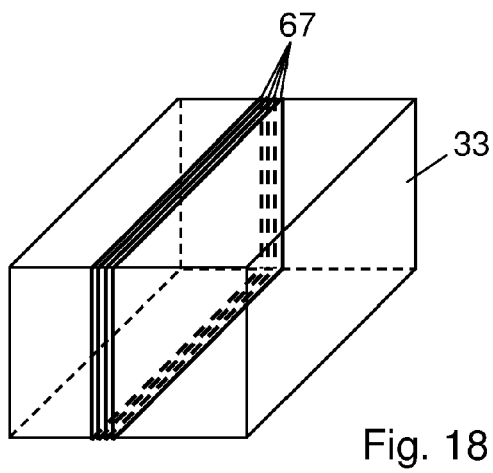

The invention and further advantageous embodiments of the invention are described in greater detail in the following by means of figures. These show as follows:

FIG. 1 an exemplary embodiment of the OCT system according to the invention;

FIG. 2 a-b) two spatial elements of a specimen with individual sections;

FIG. 3 a-b) two cross-sections through the specimen and the specimen arm of the second interferometer;

FIG. 4 a cross-section through the optical components of the second interferometer;

FIG. 5 interference signals and the evaluation of the latter with the automatic calibration of the focus tracking;

FIG. 6 a-c) Interference signals and the envelope of the latter with non-modulated and modulated intensity of the light injected into the first interferometer;

FIG. 7 an example of an electric circuit for modulating the sensitivity of the detector;

FIG. 8 an exemplary structure of a so-called Linnik interferometer;

FIG. 9 a-c) three different positions of the specimen objective and the respectively obtained interference patterns;

FIG. 10 a-b) respective sections from a longitudinal section through the multimode fibre of the first optical fibre in the region of the input plane;

FIG. 11 a section from a cross-section through the fibre bundle of the second optical fibre and a partial region of this section shown in enlarged form;

FIG. 12 a section of the detector surface;

FIG. 13 the detector surface and the inlet and outlet surface of the second optical fibre;

FIG. 14 a-b) two examples of the embodiment of the second optical fibre as cross-sections;

FIG. 15 an interference pattern and a section from the interference pattern in comparison to the individual fibres of the second optical fibre;

FIG. 16 a section from a longitudinal section through the fibre bundle of the second optical fibre in the region of the inlet surface;

FIG. 17 a detector surface in the first operating mode;

FIG. 18 a spatial element of the specimen with depth sections; and

Figure 19:
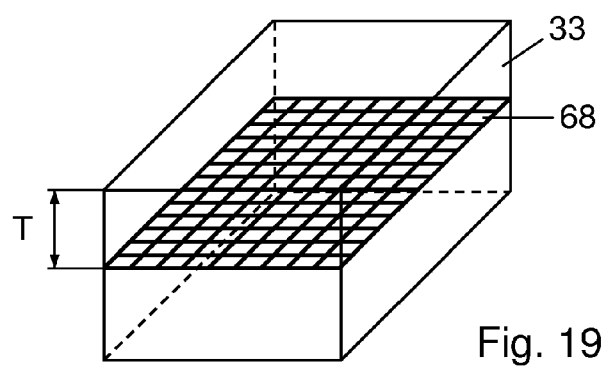

FIG. 19 a spatial element of the specimen with a two-dimensional tomogram at a specific depth.

FIG. 1 shows an exemplary embodiment of the system according to the invention for OCT. The illustration chosen here of the individual components of the system is greatly schematised and not true to scale.

A first interferometer 10 has a first reference mirror 11 in a fixed position, a moveable second reference mirror 12 and a first beam splitter 13. Light 14 from a light source 15 is injected into the first interferometer 10, split by the first beam splitter 13 into a first partial beam 2 in the direction of the first reference mirror 11 in a fixed position and a second partial beam 3 in the direction of the moveable second reference mirror 12. The two partial beams 2 and 3 are reflected by the fixed first reference mirror 11 and the moveable second reference mirror 12 and are superimposed in the first beam splitter 13 to form a third partial beam 4 which is injected into a first optical fibre 17 in the region of the output 8 of the first interferometer 10, conveyed from the latter to a second interferometer 20 and injected here into an illumination arm 21 of the second interferometer 20.

The light 14 injected into the first interferometer 10 is spectrally modulated by the optical path described in association with the movement of the second reference mirror 12 and leaves the first interferometer 10 in the form of the third partial beam 4 which is injected into the second interferometer 20. Therefore, the first interferometer 10 can also be called a pre-modulator.

The second interferometer 20 serves as a sensor or measuring head which is brought manually by an operator, for example a doctor, into contact with the specimen 1 to be examined, in particular a biological tissue, and if appropriate is moved over the latter. The measuring head is so compact in structure here that its length preferably corresponds to that of a conventional writing implement such as e.g. a fountain pen.

In order to form the second interferometer 20 in this compact manner, the optical axes of the illumination arm 21 and of a reference arm 23 in which a third reference mirror 25 is in a fixed position, are respectively tilted about 90° in relation to the conventional perpendicular arrangement of the two optical axes (see the first interferometer 10) and extend parallel to one another. In order to deflect the light beams from the illumination arm 21 and the reference arm 23 into the second beam splitter 24 a first and a second deflecting prism 26 and 28 are provided.

The first, second and third reference mirrors 11, 12 and 25 do not have to be mirrors in the narrower sense, but are to be generally considered as surfaces which at least partially reflect the light located within the first and second interferometers 10 and 12, and this is why the first, second and third reference mirrors 11, 12 and 25 can also be called the first, second and third reflectors.

The partial beams superimposed in the second beam splitter 24 pass via the specimen arm 22 of the second interferometer 20 into the specimen 1, are reflected here on boundary surfaces between media with different refraction indices, e.g. membranes or cell layers, and finally pass via the specimen arm 22 and the second beam splitter 24 into the output arm 27 from where they are injected into a second optical fibre 29 and conveyed via the latter to a detector objective 31 which images the light conveyed by the optical fibre 29 onto the surface of a two-dimensional detector 30, enlarging it.

The detector 30 is preferably a semiconductor detector in CMOS technology and has a plurality of detector elements (pixels) disposed in an area, typically 640×512 pixels. Due to the simultaneous ("parallel") recording of a plurality of reflections in different lateral positions from a plane at a specific depth of the specimen 1 made possible by this, this type of OCT can also be called "parallel OCT".

The detector signals produced upon collecting the light striking the individual detector elements of the detector 30 are further processed in an electric circuit 32 and finally forwarded to a computer system 16 for graphic display and, if required, processing.

In comparison to OCT systems with just one interferometer, with the OCT system described here the movement of the second reference mirror 12 for the spectral modulation of the injected light 14, the direct collecting of the light reflected by the specimen 1 and the recording of the image are allocated to three spatially separate components, namely to the first interferometer 10, the second interferometer 20 which constitutes the measuring head, and the detector 30.

By shifting the movement of the second reference mirror 12 and the recording of the image onto separate components, the second interferometer 20, and so the measuring head, can be designed to be very compact and easy to manage. This makes the present OCT system particularly suitable for applications at external or internal locations of a body to be examined which are very difficult to access.

In the following sections preferred embodiments of the system according to the invention and advantageous combinations of individual embodiments are described in greater detail.

1. Depth Scan by Macroscopic Movement of the Reference Mirror

The moveable second reference mirror 12 in the first interferometer 10 has an optical distance I from the first beam splitter 13 and, starting from an initial position N, implements a linear, preferably periodic, movement towards the first beam splitter 13 and away from the first beam splitter 13 with an optical path length L and amplitude A, the optical path length L and the amplitude A being at least 100 times, preferably 1000 times, greater than the average wavelength $\lambda_0$ of the light 14 injected into the first interferometer 10.

The optical distance I is given here by the product of the spatial distance between the second reference mirror 12 and the first beam splitter 13 and the refraction index of the medium located between the second reference mirror 12 and the first beam splitter 13.

With the preferred embodiment of the first interferometer 10 as a so-called free-beam interferometer described here with which air or a vacuum is to be found between the second reference mirror 12 and the first beam splitter 13 and the refraction index is approximately equal to 1, the optical distance I of the second reference mirror 12 and the optical path L by which the optical distance I is changed is identical to the spatial distance or spatial path of the latter. In this case the macroscopic change of the optical distance of the second reference mirror 12 is produced by a macroscopic movement of the second reference mirror 12 by a spatial path which is substantially greater than the average path length $\lambda_0$ of the light 14 injected into the first interferometer.

Alternatively, with an embodiment of the first interferometer 10 as a so-called fibre interferometer (not shown) between the second reference mirror 12 and the first beam splitter 13 a light-conducting element, in particular an optical fibre, can be provided the optical length of which can be changed specifically by an optical path. These optical fibres are also called fibre stretchers. In this case the optical distance or the optical path by which the optical distance is changed is given by the product of the spatial distance or the spatial path by which the distance is changed and the refraction index of the light-conducting element which typically comes within the range around 1.5.

The average wavelength $\lambda_0$ of the light 14 injected into the first interferometer 10 comes typically within the infrared spectral range, preferably between 750 and 1350 nm.

In the case of a broadband light source 15 the average wavelength $\lambda_0$ of the light 14 preferably comes within a spectral range in which the light 14 of the light source 15 has an intensity maximum. Alternatively, the average wavelength $\lambda_0$ is given by an average value of all of the wavelengths emitted by the light source 15.

Preferably, the average wavelength $\lambda_0$ of the light 14 injected into the first interferometer 10 comes within a wavelength range in which the detector 30 has a very high, in particular the highest, sensitivity. In the system illustrated, the light 14 has an average wavelength $\lambda_0$ of approximately 1300 nm and a full width at half maximum (FWHM) of approximately 200 nm.

With an average wavelength $\lambda_0$ of the light 14 in the range of e.g. 1 μm the optical wavelength L and amplitude A of the movement of the reference mirror 12 is therefore at least approximately 0.1 mm, preferably at least approximately 1 mm.

Unlike the normal microscopic amplitude of the reference mirror movement in the prior art in the order of magnitude of fractions of the average wavelength $\lambda_0$ of the injected light 14, i.e. of up to typically 1 μm, in the system described a macroscopic movement of the second reference mirror 12 in the order of magnitude of 0.1 mm to a number of millimeters is implemented.

During the macroscopic linear movement of the second reference mirror 12 the light reflected by the specimen 1 is forwarded via the second interferometer 20, the second optical fibre 29 and the detector optics 31 to the two-dimensional detector 30 and recorded by the latter successively at a number of points in time respectively for a specific period of time which corresponds to the integration time of the detector 30, and converted into corresponding detector signals.

In order for interference to be able to occur between the light reflected by the third reference mirror 25 and the light reflected by the specimen 1, the so-called coherence condition must be fulfilled which, among other things proves that the respectively reflected light waves must have a constant phase relationship with one another in order to be able to interfere with one another. Due to the use of light 14 with a very short coherence length of typically 10 μm, the condition of a constant phase relationship is only fulfilled at specific depths or depth ranges of the specimen 1 which are therefore also called a coherence gate.

Each position of the second reference mirror 12 during the macroscopic movement corresponds here to a specific depth within the specimen 1 or a depth range around this specific depth for which the coherence condition is fulfilled so that interference can occur between the light reflected by the third reference mirror 25 and the light reflected by the specimen 1.

In the case of a periodic movement of the second reference mirror 12 both half periods of the periodic movement of the second reference mirror 12 can respectively be used to record detector signals.

In this way successive two-dimensional sections are recorded from different depths of the specimen 1 by the detector 30. This is illustrated in FIG. 2 a) in which—representative of a plurality of two-dimensional sections—a first, second and third two-dimensional section 34, 35 and 36 are illustrated by a spatial element 33 of the specimen 1. This type of two-dimensional section "passes" synchronously with the macroscopic movement of the second reference mirror 12 in direction a through the examined spatial element 33 of the specimen 1 without the latter having to be moved itself.

Each section 34, 35 and 36 lies at a depth T1, T2 and T3 of the specimen 1 in which the coherence condition is respectively fulfilled so that interference can occur between the light reflected by the third reference mirror 25 and the light reflected by the specimen 1. Therefore, the macroscopic movement of the second reference mirror 12 in combination with the successive two-dimensional collection of the light reflected by the specimen 1 has the effect of a three-dimensional depth scan.

FIG. 2 b) shows in comparison to this a method used in the prior art. In order to obtain sections 37 of different depths through the spatial element 33 observed the specimen 1 itself must be moved in direction b relative to the interferometer while the absolute position of the section 38 within the space remains substantially unchanged.

In contrast to this, the combination described above of the macroscopic linear movement of the reference mirror 12 on the one hand with the collecting of the light reflected by the specimen 1 with a two-dimensional detector 30 on the other hand enables recording of a complete three-dimensional set of data for the desired spatial element 33 of the specimen 1 which is substantially easier and quicker to implement. By means of the macroscopic movement of the second reference mirror 12 a three-dimensional tomogram is thus obtained instead of an image from a specific depth which is only two-dimensional. Unlike systems according to the prior art, with this method for recording a three-dimensional set of data the specimen 1 no longer needs to be moved relative to the second interferometer 20. This makes the OCT system described compact, reliable and easy to handle, and so the latter is particularly suitable for use in vivo.

The three-dimensional set of data obtained in this way enables a precise diagnosis, in particular with biological specimens. Software-supported diagnosis aids can be used with a particularly high level of efficiency here, e.g. so-called "3D rendering" with which a three-dimensional set of data is processed by special software such that a quasi three-dimensional image is produced on a two-dimensional monitor. For this, cavities or tissue detachments, for example, can be shown as a three-dimensional animation—comparable to computer tomography (CT).

2. Focus Tracking

The OCT system described above is designed such that during a complete stroke, i.e. the wavelength L or twice the amplitude A, of the movement of the second reference mirror 12 an interference signal with sufficiently high intensity and great sharpness is always obtained. By means of the focus tracking described in greater detail in the following it is guaranteed that the interference signal and the sharpness of the interference pattern recorded are maximal for all depths within the specimen 1.

For this purpose, while collecting the light reflected by the specimen 1 the focus, i.e. the focal point of the imaging optics on the side of the specimen of the second interferometer 20 is set such that the position of the focus in the specimen 1 and the position of the plane in the specimen 1 with which, in the case of reflection of light, the coherence condition is fulfilled and interference occurs, are substantially identical at all times while recording a tomogram of the spatial element 33 of the specimen 1. This is illustrated in the following by means of FIGS. 3 a) and 3 b).

FIG. 3 a) shows the case where the focus F of the specimen objective 41—only shown in simplified form here as a lens—of the specimen arm 22 lies at a depth of the specimen 1 which does not correspond to the position of the coherence gate K. The section through the specimen 1 recorded within the coherence gate K at the depth Ti is in this way not imaged exactly sharply onto the detector 30 (see FIG. 1), and so information losses during recording of the interference have to be accepted.

On the other hand, FIG. 3 b) shows the case where the focus F of the specimen objective 41 has been set such that it comes within the coherence gate K at the depth Ti. This tracking of the focus F of the specimen objective 41 corresponding to the respective depth Ti of the coherence gate K is called focus tracking. In this way, during the depth scan the second interferometer 20 is adjusted sharply to the respective position of the coherence gate K at different depths Ti of the specimen 1 so that images with great sharpness are obtained from each depth of the specimen 1.

The maximum optical scan depth Tm specifies to which depth beneath the surface of the specimen 1 the coherence condition is fulfilled for constructive interference and corresponding interference patterns are obtained.

Moreover, by means of the focus tracking it is achieved that the illuminated surfaces on the unmoveable third reference mirror 25 in the second interferometer 20 on the one hand and at the respective depth of the specimen 1 on the other hand are identical at every depth Ti in the specimen 1 sampled. Moreover, the images of the respective illuminated surfaces via the reference arm 23 and the specimen arm 22 in the common image plane 27a of the reference and specimen arm 23 and 22 are identical and exactly superimposed.

In the following preferred embodiments of the OCT system described for the implementation of focus tracking are described in greater detail.

FIG. 4 shows a cross-section through the arrangement of the individual optical components in the second interferometer 20. The specimen objective 41 in the specimen arm 22 preferably comprises a number of lenses 42 which can be moved individually and/or in groups in direction R over the specimen 1 or away from the latter. For this purpose a piezoelectric actuator 40, in particular an ultrasound piezo motor, is provided which is coupled to the specimen objective 41 or the lenses 42 and moves the latter along one or a number of guides 38, in particular guide bars or guide grooves.

The movement of the lenses 42 preferably takes place synchronously with the macroscopic movement of the reference mirror 12 in the first interferometer 10 (see FIG. 1). In this way the focus F of the specimen objective 41 follows the coherence gate G while the latter passes through successive different depths T1, T2 and T3 of the specimen 1 from which, with the aid of the detector 30, two-dimensional sections 34, 35 and 36 (see FIG. 2) are respectively recorded.

The synchronisation of the macroscopic movement of the reference mirror 12 and the focus tracking on the one hand in combination with a two-dimensional detector 30 on the other hand guarantees particularly simple and rapid recording of a plurality of sharp, two-dimensional image sections at different depths of the specimen 1 and so the recording of a complete, three-dimensional set of image data with high image quality.

Since the first interferometer 10 and the optical imaging in the specimen arm 22 are continuously matched to one another, the interference signals recorded by the detector 30 for each depth in the specimen 1 are maximal so that a very high signal to noise ratio is produced. Moreover, in this way it is ensured that the lateral resolution for all depths in the specimen 1 is optimal because the focus F of the image always comes within the coherence gate K. In this way true-to-detail OCT images with high contrast are obtained.

Advantageously, the speed v2 of the movement of the lenses 42 of the specimen objective 41 in direction R is lower than the speed v1 of the movement of the reference mirror 12. Preferably, a ratio v1/v2 of the speeds of the reference mirror 12 and of the lenses 42 is chosen here which is approximately equal to $2 \cdot n - 1$ or up to approximately ±20%, preferably up to approximately ±10% around this value. In this way the position of the focus F and coherence gate G are matched to one another with a particularly high degree of reliability, as can be illustrated by the following consideration.

The focus F of the specimen objective 41 comes within a specimen 1 the refraction index n of which is generally not equal to one. If on the one hand one shifts the specimen objective 41 by a specific path in direction R of specimen 1, the focus F shifts within the specimen by a specific amount $d_F$. For example, the shift of the specimen objective 41 by 0.78 mm with a refraction index of the specimen 1 of 1.4 leads to a shift in the focus in the specimen 1 by approximately $d_F = 1$ mm. If, on the other hand, the reference mirror 12 is shifted by a specific path, the coherence gate K also shifts by a specific amount $d_K$. For example, a shift in the reference mirror 12 by 1.4 mm with a refraction index n=1.4 produces a shift in the coherence gate K by approximately $d_K = 1$ mm. In this way with a shift in the reference mirror 12 and the specimen objective 41 respectively by the same path, with a depth scan the coherence gate K and the focus F would move apart from one another over a macroscopic depth range.

By means of the selection described above of the ratio v1/v2 of the speeds of the reference mirror 12 and of the lenses 42 it is guaranteed that during the depth scan the coherence gate K and the focus F lie over one another in the whole depth range observed. In the above example of a specimen with a refraction index n=1.4 the ratio v1/v2 of the speeds comes within the range of approximately $(2 \cdot 1.4 - 1) \pm 20\%$, i.e. between approximately 1.44 and 2.16, and is preferably approximately $2 \cdot 1.4 - 1 = 1.8$.

The synchronisation of the movement of the reference mirror 12 and of the lenses 42 preferably takes place such that the reference mirror 12 and the lenses 42 pass at a specific point in time through two different, pre-defined spatial points at respectively constant, pre-defined and different speeds v1 and v2.

After passing through the spatial points the recording of the actual OCT signals up to the pre-defined depth in the specimen 1 starts. With a periodic forwards and backwards movement of the reference mirror 12 OCT signals can be recorded here both during the forwards and during the backwards movement of the reference mirror 12. The synchronisation of the reference mirror 12 and the lenses 42 takes place here in the same way and is re-set after each change in direction.

The measuring head in which the specimen objective 41 is located can be moved freely relative to the first interferometer 10 in which the second reference mirror 12 is located. A mechanical coupling of the specimen objective 41 and the reference mirror 12 for the synchronisation of the lens and reference mirror movements would lead to insufficient precision of the synchronisation.

Therefore, the synchronisation of the movements of the reference mirror 12 on the one hand and of the lenses 42 of the specimen objective 41 on the other hand is preferably implemented electronically. It is advantageous here to provide respectively in the region of the reference mirror 12 and the lenses 42 of the specimen objective 41a position sensor 5 and 39 which records the current reference mirror and lens position and converts this into corresponding position signals. Both position signals are supplied to a control unit, in particular the computer system 16, which then correspondingly controls the actuation of the reference mirror 12 and the lenses 42.

The control of the reference mirror 12 and of the lenses 42 is preferably implemented by feedback of the position signals by means of a so-called master-slave system. With this type of master-slave system a measured position value in a first positioning unit is the basis for a desired value of the control circuit for a second positioning unit. In the present case the measured position of the first positioning unit of the reference mirror 12 is multiplied by a factor smaller than 1 and supplied to the second positioning unit of the lenses 42 as a new desired value. In this way the relative position error between the moveable reference mirror 12 and the lenses 42 is minimised, even with a relatively large absolute positioning error of the first positioning unit. In this way both components are coupled to one another electronically, like by means of a mechanical gearing, and so this can also be called electronic gearing.

The focus tracking can alternatively or additionally be implemented by an adaptive lens being provided in the specimen objective 41 the imaging properties of which can be specifically controlled and changed. For example, an oil and water lens can be controlled electrically such that the radii of curvature of the latter change, by means of which the focus of the latter can be changed and easily be adapted to the respective position of the coherence gate. In this case the speed and the start of the change of the focus F of the adaptive lens must be synchronised with the movement of the reference mirror 12 in the same way as the methods described above.

3. Automatic Calibration of the Focus Tracking

On the specimen side end of the specimen arm 22 of the second interferometer 20 in the form of a measuring head a material layer 43 (see FIG. 4) is provided which is preferably made of sapphire glass. The material layer 43 is coated on the inside 44 with an anti-reflex layer and is preferably uncoated on the outside 45 on the specimen side.

The OCT system can be operated in a diagnosis mode and in a calibrating mode. In the diagnosis mode, which corresponds to the normal measuring operation, the specimen side outside 45 of the material layer 43 is coated with a so-called index matching gel and brought into contact with the specimen 1 to be examined, three-dimensional images of which are recorded. In the calibrating mode the position of the focus F of the specimen objective 41 relative to the coherence gate K is determined, the outside 45 of the material layer 43, which is preferably in air during the calibrating process, serves as a reference surface.

In the calibrating mode the amplitude of the OCT signal, which is caused by a reflection of the light due to the passage of the light from the material layer 43 into air, is measured for different positions of the specimen objective 41, the following procedural steps, which are illustrated by means of FIGS. 4 and 5, being implemented:

a) the group of lenses 42 is brought into an initial position by being moved as close as possible to the second beam splitter 24;
b) the group of lenses 42 is left in this position;
c) during a macroscopic movement of the second reference mirror 12 the amplitude Ai of the maximum of the interference signal is determined;
d) the group of lenses 42 is moved away by a few micrometers, typically 5 to 20 µm, from the second beam splitter 24 and kept in this position;
e) steps c) to d) are repeated for a number of different positions P1 to P11 of the lenses 42, for each position P1 to P11 of the lenses 42 an amplitude A1 to A11 of the maximum of the respective interference signal being obtained;
f) the position P9 of the group of lenses 42 where the amplitude A9 is at its greatest is established;
g) steps c) to f) are repeated close to position P9 of this maximum with a smaller step width, typically 0.5 µm to 5 µm, the position P9' of the group of lenses 42 where the amplitude A9' is at its greatest being established;

h) from the reference mirror movement assigned to this position P9' of the group of lenses 42 position Xm of the moveable reference mirror 12 where the interference signal is maximal is established.

Alternatively, the calibration can also be implemented such that the specimen objective 41 moves to the second beam splitter 24 during the calibration.

If the group of lenses 42 is located in position P9' and the reference mirror 12 in position Xm, the coherence gate and the focus position are identical. The established positions P9' and Xm are set in the diagnosis mode as the initial position of the lens or lenses or of the reflector.

In this way any changes in the OCT system are automatically corrected without any additional hardware being required for this. Even if the material layer is contaminated or coated with index matching gel, the method described would work because then the passage of the light from dirt to air or gel to air would be used. The method is very fast and only lasts for a few seconds. It can therefore be implemented frequently, by means of which high system reliability is guaranteed.

In order to further increase the precision of the calibration method described, an additional element made of glass or plastic—a so-called target—can be applied to the material layer. The method described above is then implemented for two or more depths within the additional element. In this way, not only can an offset of the reference points for the movement of the reference mirror 12 and of the lenses 42 be corrected, but also any non-linearity. With the calibrating method described above a number of reference surfaces are then used, a number of position pairs being determined for which the focus position and the coherence gate are identical. In this way, not only can a constant relative position error between the two positioning units be corrected, but any errors in the relative linearity or the relative speed of the two units can be corrected. Such errors can be produced e.g. by ageing of the position sensors 5 and 39 when, for example, the position sensitivity of one of the two position sensors 5 and 39 changes.

In summary it can be established that the dynamic synchronisation of the focus position and the coherence gate in the diagnosis mode of the OCT system described leads to a plurality of advantages with regard to image quality and reliability. With additional, in particular regular, use of the calibrating mode described this synchronisation can be guaranteed over a long period of time.

4. Modulation of the Intensity of the Light Source

With the OCT system described the interference pattern produced is recorded with the detector 30, a corresponding interference signal being produced. The sampling rate of the detector 30 for sampling the interference signal must be chosen here so that the temporal variation of the interference structure can be recorded with sufficient accuracy. This generally requires high sampling rates if high speeds are to be achieved for a depth scan.

Since the individual periods of an interference structure must generally respectively be sampled at a number of points in time, the maximum possible scan speed in the direction of the depth of the specimen 1 is dependent upon the maximum possible sampling rate of the detector 30. When using rapid detector arrays with a high level of spatial resolution, i.e. a large number of detector elements per unit of length, the maximum sampling rate is typically in the range of approximately 1 kHz. With an average wavelength of the injected light 14 of for example 850 nm this leads to a maximum speed for the depth scan of approximately 0.1 mm/s if four points per period of the interference structure are recorded.

FIG. 6 *a*) shows the development over time of a typical interference signal which is sampled at a sampling rate of respectively four sampling time points P per period. In the figure four such points within a period of the interference signal are drawn in as an example.

In order to increase the speed of the depth scan, in the present OCT system the intensity of the light 14 injected into the first interferometer 10 is temporally modulated. This modulation takes place periodically, the frequency of the latter being greater or smaller by a specific amount, preferably by up to 40%, than the Doppler frequency $f_D$ which is given by the average wavelength $\lambda_0$ of the injected light 14 and the speed v of the moveable reference mirror 12: $f_D=2v/\lambda_0$. Typical frequencies of this modulation come within the range between 1 kHz and 25 kHz.

Alternatively or additionally, the intensity of the light of the third partial beam 4 emitted by the first interferometer 10 can also be modulated with the modulation frequency $f_M$ in order to achieve the advantageous effect described above. The modulation is preferably implemented here during the injection of the light of the third partial beam 4 into the first optical fibre 17 at the output 8 of the first interferometer 10. However, the intensity modulation can also take place in the second interferometer 10 before the light of the third partial beam 4 is emitted. In order to modulate the intensity of the light emitted by the second interferometer 10 an optical element is preferably provided which is disposed e.g. in the first interferometer 10 or in the region of the output 8 of the first interferometer 10 and can be specifically changed as regards its transmission or imaging properties. Therefore, for example, by means of an adaptive optical element in the region of the output 8 of the first interferometer 10 the intensity of the light of the third partial beam 4 emitted by the first interferometer 10 can be periodically switched from "high" to "low". However, the optical element can also be disposed in the optical path of the first interferometer 10, e.g. between one of the reference mirrors 11 or 12 and the first beam splitter 13.

The definite choice of modulation frequency is made dependently upon the average wavelength $\lambda_0$ of the injected light 14 of the light source 15, the desired scan speed of the depth scan and the maximum sampling rate of the detector 30.

Preferably the modulation frequency is chosen such that it corresponds to the maximum sampling rate of the detector 30 or a whole number multiple of the latter. The maximum sampling rate is given here by the reciprocal value of the minimum frame time of the detector 30. The minimum frame time of the detector 30 is made up of the minimum time required in order to record a complete image and the minimum down time of the detector 30 which elapses until the next image can be recorded. The minimum frame time generally increases as the size of the image recorded increases.

The form of the modulation of the intensity of the light 14 is preferably sinusoidal or rectangular. The latter form can be produced e.g. simply by means of a rotating chopper wheel 18 (see FIG. 1). Other possibilities are acousto-optic or electro-optic modulators or liquid crystal modulators. A direct modulation of the light source 15 is also possible, the latter being controlled such that it emits the light 14 with temporally modulated intensity.

A corresponding effect can alternatively or additionally be achieved by an optical element, which is disposed e.g. before or after the first beam splitter 13 (see FIG. 1), being switched as to its transmission or imaging property. Therefore, for example, by correspondingly connecting an adaptive optical element the injection efficiency of the third partial beam 4 into the first optical fibre 17 could periodically be switched from "high" to "low".

The described modulation of the intensity of the injected light 14 with a modulation frequency deviating, preferably slightly, from the Doppler frequency produces a low-frequency beat frequency between the modulation and the interference signal.

FIG. 6 *b*) shows the time behaviour of a beat frequency signal obtained upon the basis of the modulation described of the injected light 14 which—like the interference signal in the example of FIG. 6 *a*)—is sampled at a sampling rate of respectively four sampling time points P per period. Upon sampling the beat frequency signal, due to the lower frequency of the latter considerably fewer sampling time points P per unit of time are required than with the sampling of the interference signal in FIG. 6 *a*) so that with a fixed sampling rate given by the choice of detector 30, considerably higher speeds can be achieved for the depth scan.

A further advantage of this method is described in greater detail in the following.

The integration time of the detector 30 corresponds to the period of time over which the detector 30 collects and thus integrates the light hitting the detector elements in the region of a time P. The detector 30 is preferably operated such that the integration time is only marginally shorter than the frame time. The frame time is chosen here such that it corresponds exactly to the duration of a period of the modulation or to a whole number multiple of the latter. The beat frequency signal shown in FIG. 6 *b*) was obtained by integration over the duration of two periods of the modulation.

If one were to increase the scan speed without modulating the intensity of the light 14 as described above, the frame time—and so the integration time—of the detector 30 would have to become shorter because the Doppler frequency would increase and in this way sampling time points P lying closer together in time would be necessary. However, a shorter integration time would lead to a reduction of the photons collected per integration and per detector element, and this would lead to a reduction in the signal/noise ratio due to the so-called Schott noise resulting from the statistical nature of the photons. In order to improve the signal/noise ratio again, the intensity of the injected light 14 would have to be increased in proportion to the scan speed.

If, on the other hand, one increases the scan speed with the aid of the modulation of the intensity of the light 14 described above, the integration time can remain constant. There is only a light loss of 50% due to the modulation of the light 14. With the preferred modulation frequency, which corresponds to twice the reciprocal value of a frame time, there is an increase by factor 8 of the speed. In this case four times less light intensity is required in order to achieve this increase in speed than in the case without modulation. The effects of the light loss amounting to 50% due to the modulation are in this way over-compensated.

With the described method, the required intensity of the light 14 of the light source 15 must—unlike direct sampling without beat frequency—therefore not be increased with the scan speed because in this case the integration time of the detector 30 can remain constant.

A further advantage of the light modulation is the reduction of the quantity of data for a complete three-dimensional depth scan. With the recording of a three-dimensional set of data with a lateral size of 512×640 pixels and a scan depth of 1 mm in a tissue with the refraction index n=1.4, approx. 6 Gbytes of data are produced. With the modulation of the intensity of the light 14 described above the quantity of data is reduced to 750 Mbytes.

Moreover, the directly obtained data must additionally be processed in order to display the image result. Here too the reduced quantity of data is very advantageous because in this way the processing time is considerably reduced, and so the image result is available more quickly.

Preferably the Doppler frequency and/or the modulation frequency are chosen such that a period of the resulting beat frequency signal is a whole number multiple of the minimum frame time of the detector 30, i.e. such that the maximum sampling rate of the detector 30 is a whole number multiple of the frequency of the beat frequency signal.

If one chooses a period length of the modulation of the light 14 as a minimum frame time of the detector 30, the scan speed increases by factor 4 in relation to the scan speed with non-modulated light 14. If, however, one chooses a minimum frame time of two periods of the modulation, the scan speed increases by the factor 8.

FIG. 6 c) shows the envelope Eu and Em of the interference signal or beat frequency signal shown in FIGS. 6 a) and 6 b) with unmodulated and modulated light 14. Each point P' of the envelope Eu and Em corresponds here to a sampling time P of the associated interference signal or beat frequency signal.

Information is deduced from the respective envelope Eu and Em from which initially one-, two- and finally three-dimensional images of the specimen 1 are put together. As trials have shown, by means of the intensity modulation implemented, despite the considerably smaller number of measuring points P and P', no relevant information losses in comparison to a conventional system without intensity modulation occur.

Overall, by means of the described modulation of the intensity of the injected light 14 the maximum possible speed of the depth scan is multiplied without any significant information losses occurring when the signal is evaluated.

5. Modulation of the Sensitivity of the Detector System

The principle of the modulation of the intensity of the light 14 injected into the first interferometer 10 and of the light of the third partial beam 4 emitted by the first interferometer described above can be analogously applied to the sensitivity of the detector system which, among other things, comprises the detector 30 and the detector objective 31 by the sensitivity of the detector system, in particular of the detector 30, being modulated for the light to be collected with a frequency which is preferably greater or smaller than the Doppler frequency $f_D$ by a specific amount, in particular by up to 40%.

The light reflected by the specimen 1 and striking the detector 30 is superimposed here with the modulated sensitivity of the detector system 30, 31 so that when recording the interference pattern striking the detector 30 the detector 30 produces, instead of a high-frequency interference signal with a plurality of periods, a low-frequency beat frequency signal which has considerably fewer periods than the high-frequency interference signal. With the sampling of this beat frequency considerably fewer sampling time points are therefore required per unit of time than with sampling of the high-frequency interference signal without the modulation of the sensitivity of the detector system 30, 31.

The sensitivity of the detector 30 can be modulated e.g. directly or with a controllable electronic shutter disposed in front of the detector 30. Alternatively or additionally, properties of an optical element in the detector system, such as e.g. the permeability of the detector objective 31, can be modulated for the light reflected by the specimen 1.

The mode of operation of the direct modulation of the sensitivity of the detector 30 is illustrated in greater detail by means of FIG. 7 which shows a greatly schematised electric circuit. Each of the detector elements 80 of a CMOS detector can be illustrated in simplified form in the equivalent circuit diagram as a photodiode 81 which is pre-stressed with a voltage U1. An ohm resistor and a capacitor are optionally connected parallel to the photodiode 81. By irradiating the detector element 80 with light, charge carriers are produced in the photodiode 81 which trigger a flow of current I1 which is added up in an accumulator 82 of an electronic integrator 83. By means of periodic switching on and off of this integration by means of a switch 84 which is controlled with the modulation frequency $f_M$, the amount of charge, and so the respectively currently recorded light intensity is modulated with the modulation frequency $f_M$. By means of a sample-and-hold step 87 the corresponding detector signal is picked up and delivered for further processing. The further switches 85 and 86 serve to control the restoration of the integration and the picking up of the detector signal.

In the same way as the modulation of the intensity of the injected or emitted light 14 and 4 described above, with this version too, instead of a high-frequency interference signal, a low-frequency beat frequency signal (see FIGS. 6 a) and b)) is obtained which can be sampled with considerably fewer sampling time points P without losing any relevant information here. With a given maximum sampling rate of the detector 30, the consequence of this is that the maximum speed for a depth scan of the system can be increased by a multiple.

As with the modulation of the injected or emitted light 14 and 4 (see section 4), here too, by means of an appropriate choice of frequency of the modulation of the sensitivity of the detector system 30, 31, the scan speed is increased by factor 4 or even 8 in comparison with systems with constant detector sensitivity.

The speed of the movement of the second reference mirror 12 is in a fixed relationship to the frequency of the modulation of the sensitivity of the detector 30 and is preferably chosen such that over a period duration of the beat frequency signal produced a whole number amount of sampling time points, preferably four sampling time points, pass (see FIG. 6 b)).

The beat frequency signals sampled in this way must be processed again before a visualisation because the interference information is also contained in these signals. The essential information which is to be visualised is the amplitude and the depth position of the respective interference, not however the interference structure itself. For this purpose the beat frequency signal must be demodulated, i.e. the envelope of the beat frequency signal is determined (see Em in FIG. 6 c)).

Since the phase of the beat frequency signal is generally unknown and this can also be different for different beat frequency signals from different depths, a digital demodulation algorithm is used which is independent of the phase. Preferably, for the sampling of the interference signal with four sampling time points per period so-called 90° phase shift algorithms are used. In this way fast demodulation of the beat frequency signal is achieved.

6. Measuring Head with Asymmetrical Linnik Interferometer

In the following the structure of the measuring head, which comprises the second interferometer 20, is illustrated in greater detail by means of FIGS. 4, 8 and 9.

The second interferometer 20 is a so-called Linnik interferometer. FIG. 8 shows an example of a typical structure of this type of Linnik interferometer with a beam splitter 77, reference mirror 78, detector 79 and specimen 70. With this type of Linnik interferometer limits are basically set for miniaturisation, and this applies in particular to the diameters of the optical elements used such as e.g. the objectives 75 and 76 and the lenses 71 and 74, and the geometric structure. The structure of the specimen and reference objective 75 and 76 and the distance q between the latter and the beam splitter 77 are substantially equal.

With the Linnik interferometer used in the present OCT system the distances between the specimen and reference objective 41 and 46 and the second beam splitter 24 (see FIG. 4) are generally not equal for all scan depths due to the focus tracking. In this way large relative optical path length differences (OPD) can occur between the image centre and the image edge of the specimen and reference image. The consequence of these can be that the spatial frequency of the interference structure to be recorded becomes greater than the resolution of the two-dimensional detector 30 due to which the interference can no longer be demonstrated, or only be demonstrated insufficiently reliably.

In order to avoid these disadvantages, in the second interferometer 20 of the present OCT system the specimen and reference objective 41 and 46 are designed differently ("asymmetrically") and matched to one another, as illustrated in greater detail below by means of FIG. 4.

The distance p between the specimen objective 41, in particular of the lenses 42, and the second beam splitter 24 is chosen to be very small. For the upper scan position in which the light reflected by a section lying close to the surface of the specimen 1 (see FIG. 2 a) is collected, the distance p is preferably between 1 and 3 mm. In this way the diameters of the lenses 42 and 49 in the specimen and reference arm 22 and 23 are chosen to be very small with at the same time a large light yield.

A further group of lenses 47 in the output arm 27 forms together with the specimen and reference objective 41 and 46 the specimen and reference optics. The specimen and reference optics are telecentric on the side of the specimen 1 and of the third reference mirror 25. Telecentric optics are characterised in that the object distance can be varied and the image size nevertheless remains constant. This is achieved by an aperture stop.

The numerical aperture for the imaging of the specimen 1 is relatively large, preferably approximately 0.3. However, the numerical aperture of the illumination of the specimen 1 is smaller than the numerical aperture for the imaging of the specimen 1, and preferably has a value of 0.2. In this way, together with the telecentric design of the specimen and reference optics one gains the advantage of the light reflected on inclined specimen structures also being picked up by the specimen objective 41 because the acceptance angle of the specimen objective 41 is greater than the divergence angle of the illumination cone. If the numerical aperture for illumination and imaging were of equal size, however, with the reflection on inclined specimen structures less light would be picked up than with the reflection on structures which are perpendicular to the optical axis.

In the specimen arm 22 the smaller numerical aperture for the illumination is provided by the choice of illumination objective 48 in the illumination arm 21. The numerical aperture in the reference arm 23 is equal to or somewhat larger than the numerical aperture of the illumination arm 21. This is particularly advantageous with the folded Linnik interferometer used here because in this way the reference objective 46 can be adapted relatively easily to the specimen objective 41 and moreover can be produced compactly.

The optical path through the lenses 49 of the reference objective 46 (including any air spaces between the lenses 49) is shorter than the optical path through the group of lenses 42 of the specimen objective 41.

By means of these measures it is possible for the image field curvatures of the specimen arm and the reference arm 22 and 23 in the centre of the used scan depth to be largely identical. Moreover, it is guaranteed that the maximum optical path length difference (OPD) between the image centre and image edge on the upper and lower end of the depth scan is small enough in order to guarantee a spatial frequency of the interference structure which is small enough in order to fulfil the Nyquist condition with regard to the detector 30. In this way the spatial frequency of the interference structures from different depths in the observed spatial element 33 of the specimen 1 is always smaller than the resolution of the two-dimensional detector 30. The interference structures are in this way always recorded with a high degree of reliability at every depth of the observed spatial element 33 of the specimen 1.

This is illustrated in FIGS. 9 a) to c) in which a specimen side section of the cross-section of the second interferometer 20 is shown at three different times during a depth scan.

At a first time (see FIG. 9 a)) the coherence gate K is in an upper layer 34 of the observed spatial element 33 of the specimen 1 (see FIG. 2 a)). Here the specimen objective 41 is a small distance away from the second beam splitter 24 and a relatively large distance away from the material layer 43 or the specimen 1. The interference structure obtained here is shown in the right-hand part of FIG. 9 a) and has a period length which corresponds to the distance between two respective consecutive light or dark rings. This period length is greater than the centre-centre distance (pitch) of the individual detector elements (pixels) of the detector 30, i.e. the spatial frequency of the interference structure, which corresponds to the reciprocal period length, is smaller than the resolution of the detector 30 which corresponds to the reciprocal centre-centre distance of the pixels of the detector 30, by means of which the so-called Nyquist condition is fulfilled. In this way it is guaranteed that the interference structure can be reliably recorded by the detector 30.

At a second time (see FIG. 9 b)) the coherence gate K is in a central layer 35 of the observed spatial element 33 of the specimen 1 (see FIG. 2 a)). The specimen objective 41 is in a position which is slightly further away from the second beam splitter 24 and somewhat closer to the material layer 43 than in FIG. 9 a)). In this case the interference structure has a greater period length than in FIG. 9 a)) so that at this time too the Nyquist condition is fulfilled.

At a third time (see FIG. 9 c)) the coherence gate K is in the deepest layer 36 of the observed spatial element 33 of the specimen 1 (see FIG. 2 a)). The specimen objective 41 is in a position which is even further away from the second beam splitter 24 and even closer to the material layer 43 than in FIG. 9 b). In this case the interference structure has approximately the same period length as at the time illustrated in FIG. 9 a) so that in this depth scan position too the Nyquist condition is fulfilled.

Due to the described asymmetrical embodiment of the specimen and reference objective 41 and 46, different distances and optical paths p and r between the specimen and reference objective 41 and 46 and the second beam splitter 24 can be produced. In the example shown, in this way the specimen objective 41 at distance p can be brought close to the second beam splitter 24, by means of which small diameters of the lenses 42 with a high light yield can be produced. At the same time the reference objective 46 can be disposed a considerably greater distance away r (r>p) from the second beam splitter 24, by means of which folding of the second interferometer 20 is made possible with which the reference and illumination arm 23 and 21 are respectively tilted about 90° in relation to their position in a non-folded Linnik interferometer (see FIG. 8) and in this way extend parallel to the specimen arm 22.

In this way a very slim form of the measuring head is produced and at the same time it is guaranteed that the image on the detector 30, which is produced by the reference and specimen optics, is of equal size and well superimposed for all scan depths.

By means of the embodiment of the reference objective 46 described above, part of the optical path which is required for folding is compensated. Therefore, the reference objective 46 is optically shorter than the specimen objective 41. In this way the embodiment of the first interferometer 10 is simpler because in this way the two interferometer arms of the first interferometer 10 do not have to differ from one another so greatly in order to fulfil the coherence condition for the occurrence of interference.

The difference between the optical path lengths in the reference and the specimen arm 23 and 22 is preferably at least twice as great as the maximum scan depth Tm (see FIGS. 3 a) and b)). The maximum optical scan depth Tm specifies up to which depth beneath the surface of the specimen 1 the coherence condition for the occurrence of interference is fulfilled and corresponding interference patterns are obtained. In this way a clear and simple assignment of the position of the reference mirror 12 in the first interferometer 10 at a specific depth in the specimen 1 is guaranteed.

7. Single Mode Pre-Modulation and Multimode Fibre

With the embodiment of the first interferometer 10 preferred here in the so-called free beam optics, when using the conventionally used spatially short or incoherent light sources a relatively complex objective is required in the region of the output 8 of the first interferometer 10 in order to inject the outgoing light as efficiently as possible into the first optical fibre 17 and thus avoid light losses. In this way not only the optical structure of the second interferometer 20, which is to be designed as compactly as possible for endoscopic applications, but also the structure of the optics of the first interferometer 10 are restricted. Moreover, if applicable, any required increase in the light output is restricted with the conventionally used spatially short or incoherent light sources.

In order to avoid these disadvantages, in the present OCT system one or a number of single mode light sources respectively having high spatial coherence, such as e.g. superluminescence diodes (SLEDs), short pulse lasers or supercontinuum lasers, are used as a light source 15. The light 14 of the light source 15 is injected into the first interferometer 10, only the so-called Gauss mode, which corresponds to a single mode, being transmitted. Only after passing through the first interferometer 10 is the spatial coherence of the injected light 14 destroyed by the light at the output 8 of the first interferometer 10 being injected into the first optical fibre 17 which has a very long multimode fibre.

A multimode fibre is a fibre the numerical aperture and characteristic diameter of which allows not just one fibre mode to be formed with a specific wavelength of the light, but makes it possible for many different fibre modes to be stimulated. Whether a fibre is a single mode fibre or a multimode fibre can be estimated using the so-called V figure V:

$$V = \frac{\pi}{\lambda} \cdot d \cdot NA$$

A specifying the wavelength of the light injected into the fibre, d the characteristic diameter of the fibre and NA the numerical aperture of the fibre. The wavelength λ of the light injected into the fibre is preferably identical here to the average wavelength $\lambda_0$ of the light 14 injected into the first interferometer. If the V figure is greater than approximately 2.4, this is a multimode fibre.

The multimode fibre preferably used in the first optical fibre 17 has typical lengths in the order of magnitude of approximately 100 m and is preferably predominantly wound onto a coil 19, as indicated in FIG. 1. The characteristic diameter of the multimode fibre is preferably between approximately 200 µm and approximately 400 µm.

The very long, thin and preferably wound up multimode fibre can optionally be combined in the first optical fibre 17 with a relatively short, thick fibre (not shown) the diameter of which comes within the range of approximately one millimeter and the length of which comes within the range of meters.

By means of the destruction of the spatial coherence of the light of the single mode light source 15, the light reflected by two different points in the specimen 1 is prevented from being able to interfere, and this is also referred to as so-called coherent cross-talk.

Moreover, efficient suppression of the coherent cross-talk leads to effective suppression of undesired scattered light which, in the case of a light source with high spatial coherence, would also contribute to interference, and consequently would lead to a blurred, washy image—similar to an image behind a pane of frosted glass. In the way described above efficient destruction of the spatial coherence is implemented, by means of which the detection of scattered light is greatly reduced and finally a sharp image is obtained.

The pre-modulation information produced in the first interferometer 10, i.e. the spectral modulation of the injected light 14 brought about by the movement of the second reference mirror 12, is not changed, however, when the light is transmitted by means of the very long multimode fibre of the first optical fibre 17. This is guaranteed in that in the multimode fibre both arms of the first interferometer 10 produce identical modes with identical mode distribution and identical phases.

Each mode itself then transmits the pre-modulation information, the individual modes not being coupled with one another. This is achieved by the first and second partial beams 2 and 3 in the first interferometer 10 (see FIG. 1) being superimposed co-linearly and exactly in relation to a third partial beam 4 before they enter into the multimode fibre of the first optical fibre 17.

The entry of the light into the multimode fibre of the first optical fibre 17 determines here the number and distribution of the modes stimulated in the multimode fibre. For particularly efficient destruction of the spatial coherence it is advantageous to chose an injection with which the largest possible number of modes are stimulated. This can be implemented in particular by—as shown in FIGS. 10 a) and 10 b)—the focus 55 of the light beams, i.e. of the third partial beam 4, not lying on the facet 9, i.e. the entry plane, of the multimode fibre of the first optical fibre 17 and/or by the light beams of the third partial beam 4 being injected at an angle into the multimode fibre of the first optical fibre 17, the optical axis 56 of the light beams being tilted in relation to the central axis 57 of the multimode fibre of the first optical fibre 17 and enclosing an angle w, which is preferably between 5° and 40°, with the latter. In this way on the one hand the spatial coherence is suppressed to the maximum, and on the other hand the illumination of the facet 9 of the multimode fibre is more homogeneous.

Moreover, in FIGS. 10 a) and 10 b) the characteristic diameter d of the multimode fibre used in the first optical fibre 17 is drawn in.

The described combination of the injection of highly-coherent light 14 into the first interferometer 10 in combination with the injection of the light of the third partial beam 4 subsequently spectrally modulated in the first interferometer 10 into the first optical fibre 17 makes it possible to form the optics very simply in the region of the output 8 of the first interferometer 10.

Since with this principle bright coherent light sources, such as e.g. SLEDs, short pulse lasers or supercontinuum lasers, can be used as a light source 15, it is possible to achieve considerably higher output densities than with the conventionally used temporally incoherent light sources. The signal/noise ratio of the image information obtained is in this way considerably improved.

Alternatively to the free beam interferometer illustrated and described here, by using this principle the first interferometer 10 can also be designed totally as a fibre interferometer. The depth scan could then be implemented e.g. instead of by means of the movement of the second reference mirror 12, by extending a fibre in one of the two arms of the first interferometer 10 by means of a so-called fibre stretcher.

8. Image Transfer by Means of Fibre Bundles

As already explained in greater detail, with the present OCT system a depth scan is implemented by means of a macroscopic movement of the reference mirror 12 in the first interferometer 10 while the light reflected by the specimen 1 is forwarded to the two-dimensional detector 30 via the second interferometer 20 and the second optical fibre 29 and collected by the latter.

A fibre bundle made up of a plurality of individual fibres is used as a second optical fibre 29. Fibre bundles generally have a high numerical aperture which is technically limited and comes within the range of 0.4 or over. Furthermore, the filling factor of the facet, i.e. the inlet or outlet cross-section, of conventional fibre bundles is relatively small. Both would lead to undesired light losses with the transmission of the light reflected by the specimen 1 from the second interferometer 20 to the detector 30.

In order to obtain the most compact possible OCT system with small light and information losses when transmitting the light reflected by the specimen 1 the fibre bundle described in greater detail in the following is used.

FIG. 11 shows a section 50 of the facet of the fibre bundle used which—as can be seen from the partial region 51 illustrated in enlarged form—is made up of a plurality of individual fibres 52 which have a centre-centre distance d2 (so-called fibre pitch).

FIG. 12 shows a section of the detector 30 used which comprises a plurality of detector elements 80 arranged in an area and which have a centre-centre distance d1 (so-called pixel pitch). With the present OCT system the fibre pitch d2 of the individual fibres 52 of the fibre bundle is smaller than the pixel pitch d1 of the detector elements 80 of the detector 30.

In order to make possible the largest possible field of vision with high spatial resolution, the fibre bundle comprises at least 100,000, preferably approximately 300,000, individual fibres 52. The number of detector elements 80 of the detector 30 is preferably approximately 328,000 and thus comes within the same order of magnitude as the number of individual fibres 52.

As shown in FIG. 13, the form of the cross-section of the fibre bundle of the second optical fibre 29 in the region of the inlet and outlet surface 7 and 6 is preferably adapted to the geometry of the detector 30, in particular the form of the inlet surface 7 on the side of the second interferometer 20 being substantially equal to the form of the outlet surface 6 on the side of the detector objective 31 and the detector 30 (see also FIG. 1). The respective form of the inlet and outlet surface 7 and 6, in particular the side length ratio of the latter, is essentially identical here to the preferably rectangular form of the detector 30.

In FIG. 14 a) two individual fibres 52 of the fibre bundle are shown as an example. The individual fibres 52 have a fibre core 65 and a fibre cladding 66. With the preferably used individual fibres 52 of the fibre bundle the ratio d3/d4 of the thicknesses d3 and d4 of the respective fibre core 65 to the fibre cladding 66 (the so-called core/cladding ratio) is chosen such that the highest possible filling factor is produced with the smallest possible light losses due to light passing out of the fibre 52 to the side (so-called evanescent waves). The filling factor here is given by the ratio of the whole cross-sectional surface of the individual fibre 52 to the surface of the fibre core 65.

With a wavelength of the light 14 of for example 1300 nm the fibre bundle used preferably has a fibre pitch d2 of 11 μm, a cladding thickness d4 of the individual fibres 52 of 1.7 μm and a core diameter d3 of 6.8 μm. The diameter of the individual fibre 52, which is produced from the sum of the core diameter d3 and twice the cladding thickness d4, is in this case 10.2 μm and is therefore somewhat smaller than the fibre pitch d2 because with the production process of the fibre bundle another second cladding (not shown) is produced around each individual fibre 52.

In FIG. 14 b) a version of the embodiment of the individual fibres 52 shown in FIG. 14 a) is illustrated. In this version the individual fibre cores 65 of the individual fibres 52 are embedded into a matrix 66 made of glass or plastic which respectively forms the fibre cladding of each individual fibre core 65. With this version two respective adjacent individual fibres 52 have part of their fibre cladding in common. The distance d4 between adjacent fibre cores 64, which corresponds to the cladding thickness, can in this way be reduced relative to the individual fibres described above with a respective own fibre cladding, the occurrence of evanescent waves furthermore being efficiently suppressed. The surface ratio of the fibre core surface to the whole fibre surface is in this way particularly large. The quotient of the core diameter d3 and the cladding thickness d4 here comes within the range between approximately 5 and 8.

The second interferometer 20 is designed such that for all scan depths a lateral interference pattern is produced the spatial frequency of which is lower than the spatial frequency of the individual fibres 52 of the fibre bundle, the Nyquist condition in particular having to be fulfilled. This is illustrated in FIG. 15. As can be seen in the enlarged section 61 of the lateral interference pattern 60, the length of a period between two consecutive interference minima 63 (dark rings) of the interference pattern 60 is greater by a multiple than the centre/centre distance (fibre pitch) of the individual fibres 52 of the fibre bundle the inlet surface 6 of which (see also FIG. 1) is illustrated here as a section and correspondingly enlarged. Correspondingly, the spatial frequency of the interference pattern 60 is considerably lower than the spatial frequency of the individual fibres 52 of the fibre bundle.

With respect to systems known from the prior art wherein the detector is incorporated into the interferometer, a number of advantages are achieved by using the fibre bundle described above which will be described in greater detail in the following.

The pixel pitch d1 of InGaAs CMOS detectors, which are sensitive to light with wavelengths within the range of approximately 1300 nm, can not be substantially smaller than 20 μm for technical reasons. The fibre bundle preferably used in the present OCT system has a fibre pitch d2 of 10 μm and therefore with the same resolution has a substantially smaller cross-section than the detector. This enables a considerably more compact design of the measuring head in comparison to systems wherein the detector is incorporated into the measuring head.

Moreover, with the aforementioned systems from the prior art, due to the very high sampling rates required of the detector, transmission of data at extremely high speed from the measuring head to the downstream electronics would be required. Moreover, A/D converters would have to be integrated into the measuring head. These disadvantages do not apply to the forwarding described here of the image information obtained from the specimen 1 by means of the second optical fibre 29 in the form of a fibre bundle to a detector 30 separate from the second interferometer 20.

Since with the present OCT system no electronics are required, therefore, in order to record and/or process the image in the measuring head, there is no lost heat which could lead to undesired heating of the measuring head.

Since in the second optical fibre 29 a fibre pitch d2 (e.g. 11 µm) is preferably chosen which is smaller than the smallest possible pixel pitch d1 (mainly larger than or equal to 20 µm) of the detector 30, an enlargement of the image obtained from the specimen 1 in the measuring head with equal lateral resolution in comparison to systems from the prior art can be reduced, and this makes more simple and smaller optics possible in the second interferometer 20.

In order to increase the light yield with the light and image information transmission from the specimen 1 or from the third reference mirror 25 to the detector 30, adaptation of the numerical apertures of individual components of the present OCT systems is provided, in particular of the apertures of the specimen objective 41 and of the lenses 47 in the output arm 27 and of the apertures of the reference objective 46 and of the fibre bundle of the second optical fibre 29, of the detector objective 31 and of the detector 30. This is described in greater detail in the following by means of FIGS. 1, 4 and 16.

FIG. 16 shows a section of the second optical fibre 29 made up of a plurality of individual fibres 52 in the region of the inlet surface 7. A convergent light bundle 58 passing out of the second interferometer 20 has an aperture angle $\alpha$ and strikes the optical fibre 29 at an angle of incidence 11 in relation to the perpendicular of the inlet surface 7. The individual fibres 52 of the second optical fibre 27 have an aperture angle $\gamma$ within which they can collect arriving light. The aperture angle $\gamma$ is given by the numerical aperture of the individual fibres 52.

In order to guarantee the highest possible light yield provision is preferably made such that the sum of the aperture angle $\alpha$ of the light bundle 58 and the angle of incidence 11 is smaller than the aperture angle $\gamma$ of the individual fibres 52 of the fibre bundle 29: $\alpha+\beta<\gamma$. In this way it is guaranteed that all of the light of the light bundle 58 which strikes an individual fibre 52 passes into the latter and is conveyed to the outlet surface 6 of the second optical fibre 29.

The aperture angle $\alpha$ and the angle of incidence $\beta$ of the light bundle 58 required for this are produced by a corresponding embodiment of the specimen and/or reference and/or output objective 41, 46 and 47. This is achieved in particular by the two objective combinations of the specimen and output objective 41/47 or the reference and output objective 46/47 imaging in enlarged form, i.e. the aperture angle $\alpha$ of the light bundle 58 in the region of the inlet surface 7 of the fibre bundle ("image side") is smaller than the aperture angle (not shown) on the side of the specimen 1 ("object side"). In this way a large aperture angle can be easily produced on the side of the specimen 1 by means of which high light collecting efficiency is achieved. Together with the loss-free injection of light into the fibre bundle of the second optical fibre 29, in this way overall a very high light yield is guaranteed when collecting the light reflected by the specimen 1, and so a high image quality is achieved.

Alternatively, or additionally, in order to increase the light yield, adaptation of the fibre bundle side numerical aperture of the detector objective 31 to the numerical aperture of the fibre bundle of the second optical fibre 29 is provided. The aperture angle of the detector objective 31 is greater here than the aperture angle $\gamma$ of the individual fibres 52 of the fibre bundle.

Preferably, the detector objective 31 is telecentric on the side of the fibre bundle. In this way the radiation characteristics of the fibre bundle can easily be allowed for. The field angle on the output surface 6 is equal to zero for every position on the output surface 6.

As the angle of incidence of the light beams onto the detector 30 increases, the light output collected by the detector 30 becomes smaller. In order to guarantee the highest possible light yield provision is therefore made such that the angle of incidence of the light beams onto the detector 30 is kept as small as possible. This is preferably achieved by enlarged imaging of the fibre bundle of the second optical fibre 29 onto the detector 30 and a telecentric design of the detector objective 31 on the side of the detector 30.

A further advantage when using the described fibre bundle for image transmission is that the overall enlargement M of the system can be split into two steps, namely into a first enlargement M1 in the measuring head, i.e. in the second interferometer 20, and a second enlargement M2 in the detector objective 31. In this way the first enlargement M1 of the objectives 41, 46 and 47 in the measuring head can be smaller than the overall enlargement M required for the nominal resolution of the OCT system. The following example is intended to illustrate this: With a pixel pitch of 20 µm, a fibre pitch of 10 µm and a nominal resolution of 2.5 µm, by means of the fibre bundle of the second optical fibre 29 formed as described above, an enlargement M1=4 is produced in the measuring head and an enlargement M2=2 in the detector objective 31 so as to obtain an overall enlargement M=M1× 2=8. Without an image transmission by means of the described fibre bundle an enlargement equal to the overall enlargement M=8 would, however, have to be produced in the measuring head.

Therefore, the advantage of using the fibre bundle described above is that the overall enlargement M does not only have to be provided by the objectives of the second interferometer 20, and so the specimen and/or reference and/or output objectives 41, 46 and 47 of the measuring head can be simpler and more space-saving in design, by means of which the measuring head can be substantially more compact in design overall.

As in the example of a second interferometer 20 shown in FIG. 4, in this way the average diameter D1 of the specimen objective 41 and of the lenses 47 of the output objective of the second interferometer 20 can preferably be chosen to be smaller than the diameter D2 of the second optical fibre 29 in the region of the inlet surface 7: D1<D2.

9. Operating Modes of the OCT System

The OCT system described above can be operated in three different operating modes. The operating modes are two real time modes, wherein OCT images of a specimen are produced at a high rate of approximately 5 to 10 images per second, and a static operating mode.

In the first operating mode, the real time mode 1, two-dimensional depth sections of the specimen 1 (so-called slices) are produced in real time. This is implemented in that as a detector 30 a CMOS camera is used which allows a so-called Window of Interest (WOI) to be set with which only one partial surface of the detector 30 is sensitive to light and converts the latter into corresponding detector signals. The reduction of the sensitive camera surface is associated with a considerable increase in the camera speed; with this setting more camera images can be produced per second than in the complete image mode.

In the real time mode 1a WOI is preferably chosen which in one direction corresponds to the whole camera length and width (e.g. 640 pixels) and in the other direction has the minimum possible number of pixels (e.g. 4 pixels) as given by the type of respective camera. In this way the speed of the camera is increased to such an extent that OCT images can be recorded in real time.

This is preferably achieved in combination with the modulation of the intensity of the light 14 or 4 injected into the first interferometer 10 and emitted by the first interferometer 10 or the modulation of the sensitivity of the detector system 30, 31 (see sections 3 and 4 above).

FIG. 17 shows a detector surface F1 which is made up of a first number N1 of detector elements 80 and has a length c1 and a width b1. With the aforementioned setting of a WOI, light is only collected by the detector elements 80 located in a partial surface F2 of the detector surface F1 and is converted into corresponding detector signals. The second number N2 of detector elements 80 of the partial surface F2 is smaller than the first number N1 of detector elements 80 of the whole detector surface F1. The lengths c1 and c2 of the detector surface F1 and partial surface F2 are of equal size, whereas the widths b1 and b2 of the detector surface F1 and partial surface F2 are different.

In the example shown the partial surface F2 is only four pixels wide, whereas the detector surface F1 is 512 pixels wide. The sensitive surface of the detector surface F1 is therefore reduced by a factor of 128, and this considerably reduces the period of time required for the recording of interference patterns and conversion of the latter into corresponding detector signals.

As shown in FIG. 18, in this example, instead of a complete three-dimensional tomogram, only four (corresponding to the four rows of pixels of the partial surface F2) two-dimensional depth sections 67 are obtained from the observed spatial element 33 of the specimen 1.

In the second operating mode, the real time mode 2, —as shown in FIG. 19—two-dimensional tomograms 68 are produced from a specific depth T of the observed spatial element 33 of the specimen 1, it being possible to choose any depth T. Here the whole detector surface F1 of the detector 30 is used for collecting the light reflected by the specimen 1 and the conversion of the latter into corresponding detector signals, only a maximum of five camera images, however, respectively being used to calculate a tomogram 68. For this purpose the first reference mirror 11 is periodically moved within the first interferometer 10 with an amplitude of approximately 1 μm, whereas up to five camera images are recorded which are then allocated to one OCT image. In this way tomograms 68 with a high repetition rate can be produced.

By means of a macroscopic movement of the second reference mirror 12, optionally in combination with the focus tracking (see section 1 and 2 above), any depth T from which the tomogram 68 is obtained can be chosen.

In the third operating mode, the static mode, a complete three-dimensional set of data is recorded with the aid of the macroscopic movement of the second reference mirror 12 in combination with the focus tracking. Details with regard to this can be taken in particular from sections 1 and 2.

By means of the different operating modes the OCT system can fulfil a whole range of different requirements. The functionalities when examining specimens, for example when locating relevant points in the specimen, are thus considerably extended.

10. Further Inventive Aspects of the System and Method for OCT

The system and method for OCT described in greater detail above has individual features or combinations of features by means of which the system and method are made simpler and more compact in design and quicker and more reliable when handling and image recording without all of the features listed in the preamble and/or characterising part of the independent claims being required. These features and combinations of features are also considered to be the invention.

The invention is considered in particular to be a system for optical coherence tomography with
  at least one interferometer for emitting light with which a specimen is irradiated, and
  a detector for collecting light which is reflected by the specimen, the system being characterised by one or a number of features which have been described in greater detail above, in particular in sections 1 to 9 and/or in connection with FIGS. 1 to 19.

The method corresponding to this system is also considered to be the invention.

Irradiation of the specimen with light emitted by the interferometer takes place either indirectly, i.e. by means of a further interferometer which is located between the interferometer and the specimen, or directly, i.e. without a further interferometer located between the interferometer and the specimen.

The collection by the detector of the light reflected by the specimen takes place either indirectly, i.e. by means of a further interferometer which is located between the specimen and the detector, or directly, i.e. without a further interferometer located between the detector and the specimen.

The invention claimed is:

1. A system for optical coherence tomography comprising:
  an interferometer which has a beam splitter, a reflector, an illumination arm, a specimen arm, an outlet arm and a reference arm, light being injected into the interferometer by the illumination arm and split by the beam splitter into a partial beam extending through the reference arm towards the reflector and a partial beam extending through the specimen arm towards the specimen, the partial beams being reflected by the reflector and by the specimen, respectively, and the reflected partial beams being superposed in the beam splitter to form a further partial beam, the light of which can be collected by a detector,
  a specimen objective provided in the specimen arm by means of which light of the partial beam extending through the specimen arm is focussed in a focus lying on or in the specimen, and
  a reference objective provided in the reference arm by means of which light of the partial beam extending through the reference arm is focussed onto the reflector, the optical properties of the specimen objective differing from the optical properties of the reference objective, and one or both of:
  a) a detector provided for collecting an interference pattern of the light of the further partial beam at which the partial beams reflected by the reflector and by the specimen are superposed, the interference pattern comprising a number of interference minima and interference maxima in the form of dark rings and light rings, respectively, wherein the detector comprises a plurality of detector elements, two respective adjacent detector elements having a centre-centre distance, the specimen objective comprising a group of lenses and the reference objective comprising lenses, wherein the optical path length through the lenses of the reference objective, including any air spaces between the lenses, is shorter than the optical path length through the group of lenses of the specimen objective, whereby the distance between two consecutive interference minima or interference maxima in the form of two consecutive dark rings or light rings, respectively, of the interference pattern occurring is larger for all scan depths than the centre-centre distance between the detector elements, or (b) the illumination arm comprising an illumination objective and together with the specimen or the reference objective forming an illumination optics exhibiting a numerical aperture, and the outlet arm comprising an output objective and together with the specimen objective forming a specimen optics exhibiting a numerical aperture, wherein the numerical aperture of the illumination optics is smaller than the numerical aperture of the specimen optics.

2. The system according to claim 1, wherein the specimen objective has a first focal distance and the reference objective a second focal distance, the first focal distance differing from the second focal distance.

3. The system according to claim 1, wherein the difference between the optical paths through the reference objective and the specimen objective is at least twice as large as a maximum optical scan depth in the specimen with which interference occurs between the partial beam reflected at the maximum optical scan depth in the specimen and the partial beam reflected by the reflector.

4. The system according to claim 1, wherein the position of the specimen objective relative to the beam splitter differs from the position of the reference objective relative to the beam splitter.

5. The system according to claim 4, wherein the optical path between the reference objective and the beam splitter is larger than the optical path between the specimen objective and the beam splitter.

6. The system according to claim 1, wherein the specimen objective is mounted moveably in the specimen arm so that the distance between the specimen objective and the beam splitter can be changed.

7. The system according to claim 1, wherein at least part of the optical axis of the reference arm or of the illumination arm, or of both the reference arm and the illumination arm encloses an angle, which is different from 90°, with the optical axis of the specimen arm.

8. The system according to claim 1, at least part of the optical axis of the reference arm or of the illumination arm extending parallel to the optical axis of the specimen arm.

9. The system according to claim 8, wherein a deflection element is provided in the reference arm, the illumination arm or both.

10. The system according to claim 9, wherein the deflection element comprises a deflection prism.

11. The system according to claim 1, wherein the outlet arm together with the reference objective forms reference optics, and wherein the specimen optics or the reference optics, or both are telecentric.

12. The system according to claim 1, wherein the specimen objective has a larger numerical aperture than the reference objective.

* * * * *